US008557247B2

(12) United States Patent
Lemoine

(10) Patent No.: US 8,557,247 B2
(45) Date of Patent: Oct. 15, 2013

(54) LYOPHILISED ANTIGEN COMPOSITION

(75) Inventor: Dominique Ingrid Lemoine, Rixensart (BE)

(73) Assignee: GlaxoSmithKline Biologicals SA, Rixenrart (BE)

(*) Notice: Subject to any disclaimer, the term of this patent is extended or adjusted under 35 U.S.C. 154(b) by 0 days.

(21) Appl. No.: 12/946,171

(22) Filed: Nov. 15, 2010

(65) Prior Publication Data
US 2011/0059163 A1    Mar. 10, 2011

Related U.S. Application Data

(62) Division of application No. 12/125,182, filed on May 22, 2008, now abandoned.

(30) Foreign Application Priority Data

May 24, 2007 (EP) .................. PCT/EP2007/055037
Nov. 23, 2007 (GB) .................................. 0723044.4
Dec. 6, 2007 (GB) .................................. 0723900.7

(51) Int. Cl.
A61K 38/00 (2006.01)
A61K 39/00 (2006.01)

(52) U.S. Cl.
USPC .................. 424/184.1; 424/192.1; 424/277.1; 514/1.1

(58) Field of Classification Search
None
See application file for complete search history.

(56) References Cited

U.S. PATENT DOCUMENTS

| 4,912,094 | A | 3/1990 | Myers et al. |
| 4,963,484 | A | 10/1990 | Kufe |
| 5,057,540 | A | 10/1991 | Kensil et al. |
| 5,278,302 | A | 1/1994 | Caruthers et al. |
| 5,654,140 | A | 8/1997 | Persico et al. |
| 5,666,153 | A | 9/1997 | Copeland |
| 5,744,144 | A | 4/1998 | Finn et al. |
| 5,827,666 | A | 10/1998 | Finn et al. |
| 5,830,753 | A | 11/1998 | Coulie et al. |
| 5,981,215 | A | 11/1999 | Meissner et al. |
| 6,054,438 | A | 4/2000 | Taylor-Papadimitriou et al. |
| 6,207,646 | B1* | 3/2001 | Krieg et al. ................. 514/44 R |
| 6,949,520 | B1 | 9/2005 | Hartmann et al. |
| 7,049,302 | B1 | 5/2006 | Kensil |
| 2003/0171261 | A1* | 9/2003 | Livingston et al. ............. 514/8 |
| 2004/0018204 | A1 | 1/2004 | Gaiger et al. |
| 2004/0022814 | A1 | 2/2004 | O'Hagan et al. |
| 2004/0208850 | A1* | 10/2004 | Ellenhorn et al. ........... 424/93.2 |
| 2008/0081050 | A1* | 4/2008 | Hermand et al. .......... 424/244.1 |

FOREIGN PATENT DOCUMENTS

| EP | 468520 | 1/1992 |
| EP | 1547581 | 6/2005 |
| WO | 88/05054 | 7/1988 |
| WO | 91/18926 | 12/1991 |
| WO | 95/20600 | 8/1995 |
| WO | 95/26204 | 10/1995 |
| WO | 96/02555 | 2/1996 |
| WO | 98/50567 | 11/1998 |
| WO | 99/33488 | 7/1999 |
| WO | 99/67384 | 12/1999 |
| WO | 00/44899 | 8/2000 |
| WO | 00/53748 | 9/2000 |
| WO | 01/62778 | 8/2001 |
| WO | 02/078637 | 10/2002 |
| WO | 03/025003 | 3/2003 |
| WO | 03/057822 | 7/2003 |
| WO | 2005/039630 | 6/2005 |
| WO | 2005/105139 | 10/2005 |
| WO | 2005/112991 | 12/2005 |
| WO | 2006/013106 | 2/2006 |
| WO | 2006/092017 | 9/2006 |

OTHER PUBLICATIONS

Bresnahan et al., A dileucine motif in HIV-1 Nef acts as an internalization signal for CD4 downregulation and binds the AP-1 clathrin adaptor, Current Biology 8:1235-1238 (Oct. 26, 1998).
Davis et al., CpG DNA is a potent enhancer of specific immunity in mice immunized with recombinant Hepatitis B surface antigen, J. of Immunology 160:870-876 (1998).
Griner et al., Simulatneous expression of different immunogenic antigens in acute myeloid leukemia, Experimental Hematology 28:1413-1422 (2000).
Johnson et al., Characterization of Nontoxic Monophosphoryl Lipid A, Review of Infectious Disease 9(55):5512-S516 (Oct. 1987).
Krieg et al., CpG motifs in bacterial DNA trigger direct B-cell activation, Nature 374:546 (1995).
Lu et al., a novel gene (PLU-1) containing highly conserved putative DNA/Chromatin binding motifs is specifically up-regulated in breast cancer, The J. of Biological Chemstry 274(22):15633-15645 (May 28, 1999).
Lüderitz et al., Structural relationships of Salmonella O and R antigens, Annals-New York Academy of Science 133:349 (1966).
McCluskie and Davis, Cutting Edge: CpG DNA is a potent enhancer of systemic and nucosal immune responses against Hepatitis B surface antigen with intranasal administration to mice, J. of Immunology 161:4463-4466 (1998).
Salomon et al., Cripto: a novel epidermal growth factor (EGF)-related peptide in mammary gland development and neoplasia, BioEssays 21:61-70 (1999).
Shalka, Introduction, Adv. In Virus Res., 52:271-273 (1999).
Blazer et al., Blood, 2001, 98:4, p. 1217-1225.

(Continued)

*Primary Examiner* — Albert Navarro
(74) *Attorney, Agent, or Firm* — Michael M. Conqer

(57) ABSTRACT

The present invention provides lyophilised compositions comprising an antigen and a Toll-like receptor (TLR) 9 agonist. Such compositions may be reconstituted into immunogenic compositions for use in vaccination with a carrier selected from the group of particulate carriers consisting of liposomes, mineral salts, emulsions, polymers and ISCOMs. Methods of making immunogenic compositions from the lyophilised compositions of the invention and use of the same in immunisation are also herein provided.

20 Claims, 9 Drawing Sheets

(56) References Cited

OTHER PUBLICATIONS

Baren Van et al., Tumoral and Immunologic Response, J. Clinical Oncology, vol. 22, No. 35, pp. 9008-9021, Dec. 2005.

Barrett et al., Translational Mini-Review Series on Vaccines: Peptide Vaccines for Myeloid Leukaemias, Clinical and Experimental Immunology, vol. 148(2) pp. 189-198, 2007.

Boon, et al., Monitoring CTL Responses in Melanoma Patients Vaccinated with MAGE Antigenic Peptides, European J Cancer, No. 38, S11 2001.

Coulie, et al., A Monoclonal Cytolytic T-Lymphocyte Response Ovserved in a Melanoma Patient Vaccinated with A Tumor Specific Antigenic Peptide Encoded by Gene MAGE-3, PNAS, vol. 98, No. 18, pp. 10291-10295, Aug. 2001.

Ge, et al., Antrhax Vaccine Powder Formulations for Nasal Mucosal Delivery, Journal of Pharmaceutical Sciences, J. Pharmaceuitcal Scienes, Vol. 95, No. 1, pp. 80-96, 2006.

Kruit, et al., Phase 1/2 Study of Subcutaneous and Intradermal Immunication with a Recombinant MAGE-3 Protein in Patietns with Detectable Metastic Melanoma, International J Cancer, vol. 117, pp. 594-604, 2005.

Marchand et al., Tumor Regressions Observed in Patients with Metastatic Melanoma Treated with an Antigenic Peptide Encoded by Gene Mage-3 and Presented by HLA-A1, International Journal Cancer, vol. 80, No. 2, pp. 219-230, 1999.

Mikszta et al., Protective Immunization Against Inhalational Anthrax. A Comparison of Minimally Invasive Delivery Platforms; J. Infectious Diseases, vol. 191; pp. 278-288, 2004.

Toungouz et al., Antitumor Vaccines Using Dendritic Cells Pulsed with MAGE Peptides, European Journal of Cancer, vol. 35, Suppl. 5, S1-S25, 1999.

Toungouz, et al., Transient Expansion of Peptide-Specific Lymphocytes Producing IFN-y after Vaccination with Dendritic Cells Pulsed with MAGE Peptides in Patients with MAGE-A1/A3—Postive Tumors, Journal Leukocyte Biology, vol. 69, No. 6, pp. 937-943, 2001.

\* cited by examiner

Figure 5

LipoD1/3 - MAGE3 – HIS protein :

| N term | MDP | protD 1/3 | Met ASP | Mage 3 | GlyGly 7xHis | C term |
|---|---|---|---|---|---|---|
| | 2 | 124 | 3 | 314 | | |

SEQ ID NO:13

*MD*<u>PKTLALSLLAAGVLAG</u>CSSHSSNMANTQMKSDKIIIAH 40
RGASGYLPEHTLESKALAFAQQADYLEQDLAMTKDGRLVV 80
IHDHFLDGLTDVAKKFPHRHRKDGRYYVIDFTLKEIQSLE 120
MTENFET*MD*<u>LEQRSQHCKPEEGLEARGEALGLVGAQAPAT</u> 160
<u>EEQEAASSSSTLVEVTLGEVPAAESPDPPQSPQGASSLPT</u> 200
<u>TMNYPLWSQSYEDSSNQEEEGPSTFPDLESEFQAALSRKV</u> 240
<u>AELVHFLLLKYRAREPVTKAEMLGSVVGNWQYFFPVIFSK</u> 280
<u>ASSSLQLVFGIELMEVDPIGHLYIFATCLGLSYDGLLGDN</u> 320
<u>QIMPKAGLLIIVLAIIAREGDCAPEEKIWEELSVLEVFEG</u> 360
<u>REDSILGDPKKLLTQHFVQENYLEYRQVPGSDPACYEFLW</u> 400
<u>GPRALVETSYVKVLHHMVKISGGPHISYPPLHEWVLREGE</u> 440
E*GG*<u>HHHHHHH</u>. 451

Underlined = signal sequence 15aa
Bold = first 109 amino acids of Protein D
Italics = unrelated amino acids
    * (MDP first aa of Influenza)
    * (Met-Asp at aa 128-129 to create a cloning site))
    * (Gly-Gly at 442-443).
Double underlined = fragment of MAGE3; amino acids 3-314 of MAGE3 (312 aas total)
Bold/underlined = 7 his tail − CpG + CpG

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 1
tccatgacgt tcctgacgtt                                                    20

<210> SEQ ID NO 2
<211> LENGTH: 18
<212> TYPE: DNA
<213> ORGANISM: Artificial Sequence
<220> FEATURE:
<223> OTHER INFORMATION: Immunostimulatory oligonucleotide

<400> SEQUENCE: 2
tctcccagcg tgcgccat                                                      18

<210> SEQ ID NO 3
<211> LENGTH: 30
<212> TYPE: DNA
<213> ORGANISM: Artificial Sequence
<220> FEATURE:
<223> OTHER INFORMATION: Immunostimulatory oligonucleotide

<400> SEQUENCE: 3
accgatgacg tcgccggtga cggcaccacg                                         30

<210> SEQ ID NO 4
<211> LENGTH: 24
<212> TYPE: DNA
<213> ORGANISM: Artificial Sequence
<220> FEATURE:
<223> OTHER INFORMATION: Immunostimulatory oligonucleotide

<400> SEQUENCE: 4
tcgtcgtttt gtcgttttgt cgtt                                               24

<210> SEQ ID NO 5
<211> LENGTH: 20
<212> TYPE: DNA
<213> ORGANISM: Artificial Sequence
```

<220> FEATURE:
<223> OTHER INFORMATION: Immunostimulatory oligonucleotide

<400> SEQUENCE: 5
tccatgacgt tcctgatgct                                                  20

<210> SEQ ID NO 6
<211> LENGTH: 514
<212> TYPE: PRT
<213> ORGANISM: Artificial Sequence
<220> FEATURE:
<223> OTHER INFORMATION: ENV gp120

<400> SEQUENCE: 6

Met Lys Val Lys Glu Thr Arg Lys Asn Tyr Gln His Leu Trp Arg Trp
1               5                   10                  15

Gly Thr Met Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Tyr Phe Asn Met Trp Lys
                85                  90                  95

Asn Asn Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Asp Asp Val Asn Thr Thr Asn Ser Thr Thr Thr Ser Asn
    130                 135                 140

Gly Trp Thr Gly Glu Ile Arg Lys Gly Glu Ile Lys Asn Cys Ser Phe
145                 150                 155                 160

Asn Ile Thr Thr Ser Ile Arg Asp Lys Val Gln Lys Glu Tyr Ala Leu
                165                 170                 175

Phe Tyr Asn Leu Asp Val Val Pro Ile Asp Asp Asn Ala Thr Thr
            180                 185                 190

Lys Asn Lys Thr Thr Arg Asn Phe Arg Leu Ile His Cys Asn Ser Ser
        195                 200                 205

Val Met Thr Gln Ala Cys Pro Lys Val Ser Phe Glu Pro Ile Pro Ile
    210                 215                 220

His Tyr Cys Ala Pro Ala Gly Phe Ala Ile Leu Lys Cys Asn Asn Lys
225                 230                 235                 240

Thr Phe Asp Gly Lys Gly Leu Cys Thr Asn Val Ser Thr Val Gln Cys
                245                 250                 255

Thr His Gly Ile Arg Pro Val Val Ser Thr Gln Leu Leu Leu Asn Gly
            260                 265                 270

Ser Leu Ala Glu Glu Glu Val Val Ile Arg Ser Asp Asn Phe Met Asp
        275                 280                 285

Asn Thr Lys Thr Ile Ile Val Gln Leu Asn Glu Ser Val Ala Ile Asn
    290                 295                 300

Cys Thr Arg Pro Asn Asn Asn Thr Arg Lys Gly Ile His Ile Gly Pro
305                 310                 315                 320

Gly Arg Ala Phe Tyr Ala Ala Arg Lys Ile Ile Gly Asp Ile Arg Gln
                325                 330                 335

```
Ala His Cys Asn Leu Ser Arg Ala Gln Trp Asn Asn Thr Leu Lys Gln
            340                 345                 350

Ile Val Ile Lys Leu Arg Glu His Phe Gly Asn Lys Thr Ile Lys Phe
            355                 360                 365

Asn Gln Ser Ser Gly Gly Asp Pro Glu Ile Val Arg His Ser Phe Asn
            370                 375                 380

Cys Gly Gly Glu Phe Phe Tyr Cys Asp Thr Thr Gln Leu Phe Asn Ser
385                 390                 395                 400

Thr Trp Asn Gly Thr Glu Gly Asn Asn Thr Glu Gly Asn Ser Thr Ile
                405                 410                 415

Thr Leu Pro Cys Arg Ile Lys Gln Ile Ile Asn Met Trp Gln Glu Val
            420                 425                 430

Gly Lys Ala Met Tyr Ala Pro Pro Ile Gly Gly Gln Ile Arg Cys Ser
            435                 440                 445

Ser Asn Ile Thr Gly Leu Leu Leu Thr Arg Asp Gly Gly Thr Glu Gly
            450                 455                 460

Asn Gly Thr Glu Asn Glu Thr Glu Ile Phe Arg Pro Gly Gly Gly Asp
465                 470                 475                 480

Met Arg Asp Asn Trp Arg Ser Glu Leu Tyr Lys Tyr Lys Val Val Lys
                485                 490                 495

Val Glu Pro Leu Gly Val Ala Pro Thr Arg Ala Lys Arg Arg Val Val
            500                 505                 510

Gln Arg

<210> SEQ ID NO 7
<211> LENGTH: 674
<212> TYPE: PRT
<213> ORGANISM: Artificial Sequence
<220> FEATURE:
<223> OTHER INFORMATION: Env gp140

<400> SEQUENCE: 7

Met Arg Val Met Glu Ile Gln Arg Asn Cys Gln His Leu Leu Arg Trp
1               5                   10                  15

Gly Ile Met Ile Leu Gly Met Ile Ile Cys Ser Thr Ala Asp Asn
            20                  25                  30

Leu Trp Val Thr Val Tyr Tyr Gly Val Pro Val Trp Arg Asp Ala Glu
            35                  40                  45

Thr Thr Leu Phe Cys Ala Ser Asp Ala Lys Ala Tyr Ser Thr Glu Lys
        50                  55                  60

His Asn Val Trp Ala Thr His Ala Cys Val Pro Thr Asp Pro Asn Pro
65                  70                  75                  80

Gln Glu Ile Pro Leu Asp Asn Val Thr Glu Glu Phe Asn Met Trp Lys
                85                  90                  95

Asn Asn Met Val Asp Gln Met His Glu Asp Ile Ile Ser Leu Trp Asp
            100                 105                 110

Gln Ser Leu Lys Pro Cys Val Gln Leu Thr Pro Leu Cys Val Thr Leu
            115                 120                 125

Asn Cys Ser Asn Ala Arg Val Asn Ala Thr Phe Asn Ser Thr Glu Asp
        130                 135                 140

Arg Glu Gly Met Lys Asn Cys Ser Phe Asn Met Thr Thr Glu Leu Arg
145                 150                 155                 160

Asp Lys Lys Gln Gln Val Tyr Ser Leu Phe Tyr Arg Leu Asp Ile Glu
                165                 170                 175

Lys Ile Asn Ser Ser Asn Asn Ser Glu Tyr Arg Leu Val Asn Cys
            180                 185                 190
```

```
Asn Thr Ser Ala Ile Thr Gln Ala Cys Pro Lys Val Thr Phe Glu Pro
            195                 200                 205

Ile Pro Ile His Tyr Cys Ala Pro Ala Gly Phe Ala Ile Leu Lys Cys
            210                 215                 220

Asn Asp Thr Glu Phe Asn Gly Thr Gly Pro Cys Lys Asn Val Ser Thr
225                 230                 235                 240

Val Gln Cys Thr His Gly Ile Lys Pro Val Val Ser Thr Gln Leu Leu
            245                 250                 255

Leu Asn Gly Ser Leu Ala Glu Arg Glu Val Arg Ile Arg Ser Glu Asn
            260                 265                 270

Ile Ala Asn Asn Ala Lys Asn Ile Ile Val Gln Phe Ala Ser Pro Val
            275                 280                 285

Lys Ile Asn Cys Ile Arg Pro Asn Asn Asn Thr Arg Lys Ser Tyr Arg
            290                 295                 300

Ile Gly Pro Gly Gln Thr Phe Tyr Ala Thr Asp Ile Val Gly Asp Ile
305                 310                 315                 320

Arg Gln Ala His Cys Asn Val Ser Arg Thr Asp Trp Asn Asn Thr Leu
            325                 330                 335

Arg Leu Val Ala Asn Gln Leu Arg Lys Tyr Phe Ser Asn Lys Thr Ile
            340                 345                 350

Ile Phe Thr Asn Ser Ser Gly Gly Asp Leu Glu Ile Thr Thr His Ser
            355                 360                 365

Phe Asn Cys Gly Gly Glu Phe Phe Tyr Cys Asn Thr Ser Gly Leu Phe
            370                 375                 380

Asn Ser Thr Trp Thr Thr Asn Asn Met Gln Glu Ser Asn Asp Thr Ser
385                 390                 395                 400

Asn Gly Thr Ile Thr Leu Pro Cys Arg Ile Lys Gln Ile Ile Arg Met
            405                 410                 415

Trp Gln Arg Val Gly Gln Ala Met Tyr Ala Pro Pro Ile Glu Gly Val
            420                 425                 430

Ile Arg Cys Glu Ser Asn Ile Thr Gly Leu Ile Leu Thr Arg Asp Gly
            435                 440                 445

Gly Asn Asn Asn Ser Ala Asn Glu Thr Phe Arg Pro Gly Gly Gly Asp
            450                 455                 460

Ile Arg Asp Asn Trp Arg Ser Glu Leu Tyr Lys Tyr Lys Val Val Lys
465                 470                 475                 480

Ile Glu Pro Leu Gly Val Ala Pro Thr Arg Ala Lys Arg Arg Val Val
            485                 490                 495

Glu Arg Glu Lys Arg Ala Val Gly Ile Gly Ala Val Phe Leu Gly Phe
            500                 505                 510

Leu Gly Ala Ala Gly Ser Thr Met Gly Ala Ala Ser Ile Thr Leu Thr
            515                 520                 525

Val Gln Ala Arg Gln Leu Leu Ser Gly Ile Val Gln Gln Ser Asn
            530                 535                 540

Leu Leu Arg Ala Ile Glu Ala Gln Gln Leu Leu Lys Leu Thr Val
545                 550                 555                 560

Trp Gly Ile Lys Gln Leu Gln Ala Arg Val Leu Ala Val Glu Arg Tyr
            565                 570                 575

Leu Arg Asp Gln Gln Leu Leu Gly Ile Trp Gly Cys Ser Gly Lys Leu
            580                 585                 590

Ile Cys Thr Thr Asn Val Pro Trp Asn Ser Ser Trp Ser Asn Lys Ser
            595                 600                 605

Tyr Asp Asp Ile Trp Gln Asn Met Thr Trp Leu Gln Trp Asp Lys Glu
```

```
                610                 615                 620
Ile Ser Asn Tyr Thr Asp Ile Ile Tyr Ser Leu Ile Glu Glu Ser Gln
625                 630                 635                 640

Asn Gln Gln Glu Lys Asn Glu Gln Asp Leu Leu Ala Leu Asp Lys Trp
                645                 650                 655

Ala Asn Leu Trp Asn Trp Phe Asp Ile Ser Lys Trp Leu Trp Tyr Ile
                660                 665                 670

Arg Ser

<210> SEQ ID NO 8
<211> LENGTH: 1067
<212> TYPE: PRT
<213> ORGANISM: Artificial Sequence
<220> FEATURE:
<223> OTHER INFORMATION: Gag-RT-Nef fusion

<400> SEQUENCE: 8

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300
```

```
Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Met Gly Pro Ile Ser
        355                 360                 365

Pro Ile Glu Thr Val Pro Val Lys Leu Lys Pro Gly Met Asp Gly Pro
    370                 375                 380

Lys Val Lys Gln Trp Pro Leu Thr Glu Glu Lys Ile Lys Ala Leu Val
385                 390                 395                 400

Glu Ile Cys Thr Glu Met Glu Lys Glu Gly Lys Ile Ser Lys Ile Gly
                405                 410                 415

Pro Glu Asn Pro Tyr Asn Thr Pro Val Phe Ala Ile Lys Lys Lys Asp
                420                 425                 430

Ser Thr Lys Trp Arg Lys Leu Val Asp Phe Arg Glu Leu Asn Lys Arg
            435                 440                 445

Thr Gln Asp Phe Trp Glu Val Gln Leu Gly Ile Pro His Pro Ala Gly
    450                 455                 460

Leu Lys Lys Lys Lys Ser Val Thr Val Leu Asp Val Gly Asp Ala Tyr
465                 470                 475                 480

Phe Ser Val Pro Leu Asp Glu Asp Phe Arg Lys Tyr Thr Ala Phe Thr
                485                 490                 495

Ile Pro Ser Ile Asn Asn Glu Thr Pro Gly Ile Arg Tyr Gln Tyr Asn
                500                 505                 510

Val Leu Pro Gln Gly Trp Lys Gly Ser Pro Ala Ile Phe Gln Ser Ser
            515                 520                 525

Met Thr Lys Ile Leu Glu Pro Phe Arg Lys Gln Asn Pro Asp Ile Val
    530                 535                 540

Ile Tyr Gln Tyr Met Asp Asp Leu Tyr Val Gly Ser Asp Leu Glu Ile
545                 550                 555                 560

Gly Gln His Arg Thr Lys Ile Glu Glu Leu Arg Gln His Leu Leu Arg
                565                 570                 575

Trp Gly Leu Thr Thr Pro Asp Lys Lys His Gln Lys Glu Pro Pro Phe
                580                 585                 590

Leu Lys Met Gly Tyr Glu Leu His Pro Asp Lys Trp Thr Val Gln Pro
            595                 600                 605

Ile Val Leu Pro Glu Lys Asp Ser Trp Thr Val Asn Asp Ile Gln Lys
    610                 615                 620

Leu Val Gly Lys Leu Asn Trp Ala Ser Gln Ile Tyr Pro Gly Ile Lys
625                 630                 635                 640

Val Arg Gln Leu Cys Lys Leu Leu Arg Gly Thr Lys Ala Leu Thr Glu
                645                 650                 655

Val Ile Pro Leu Thr Glu Glu Ala Glu Leu Glu Leu Ala Glu Asn Arg
                660                 665                 670

Glu Ile Leu Lys Glu Pro Val His Gly Val Tyr Tyr Asp Pro Ser Lys
            675                 680                 685

Asp Leu Ile Ala Glu Ile Gln Lys Gln Gly Gln Gly Gln Trp Thr Tyr
    690                 695                 700

Gln Ile Tyr Gln Glu Pro Phe Lys Asn Leu Lys Thr Gly Lys Tyr Ala
705                 710                 715                 720

Arg Met Arg Gly Ala His Thr Asn Asp Val Lys Gln Leu Thr Glu Ala
                725                 730                 735
```

| | | | | | | | | | | | |
|---|---|---|---|---|---|---|---|---|---|---|---|
| Val | Gln | Lys | Ile | Thr | Thr | Glu | Ser | Ile | Val | Ile | Trp | Gly | Lys | Thr | Pro |
| | | | 740 | | | | | 745 | | | | 750 | | | |

Val Gln Lys Ile Thr Thr Glu Ser Ile Val Ile Trp Gly Lys Thr Pro
                    740                 745                 750

Lys Phe Lys Leu Pro Ile Gln Lys Glu Thr Trp Glu Thr Trp Trp Thr
            755                 760                 765

Glu Tyr Trp Gln Ala Thr Trp Ile Pro Glu Trp Glu Phe Val Asn Thr
770                 775                 780

Pro Pro Leu Val Lys Leu Trp Tyr Gln Leu Glu Lys Glu Pro Ile Val
785                 790                 795                 800

Gly Ala Glu Thr Phe Tyr Val Asp Gly Ala Ala Asn Arg Glu Thr Lys
                805                 810                 815

Leu Gly Lys Ala Gly Tyr Val Thr Asn Arg Gly Arg Gln Lys Val Val
            820                 825                 830

Thr Leu Thr Asp Thr Thr Asn Gln Lys Thr Glu Leu Gln Ala Ile Tyr
        835                 840                 845

Leu Ala Leu Gln Asp Ser Gly Leu Glu Val Asn Ile Val Thr Asp Ser
850                 855                 860

Gln Tyr Ala Leu Gly Ile Ile Gln Ala Gln Pro Asp Gln Ser Glu Ser
865                 870                 875                 880

Glu Leu Val Asn Gln Ile Ile Glu Gln Leu Ile Lys Lys Glu Lys Val
                885                 890                 895

Tyr Leu Ala Trp Val Pro Ala His Lys Gly Ile Gly Gly Asn Glu Gln
            900                 905                 910

Val Asp Lys Leu Val Ser Ala Gly Ile Arg Lys Val Leu Met Val Gly
        915                 920                 925

Phe Pro Val Thr Pro Gln Val Pro Leu Arg Pro Met Thr Tyr Lys Ala
930                 935                 940

Ala Val Asp Leu Ser His Phe Leu Lys Glu Lys Gly Gly Leu Glu Gly
945                 950                 955                 960

Leu Ile His Ser Gln Arg Arg Gln Asp Ile Leu Asp Leu Trp Ile Tyr
                965                 970                 975

His Thr Gln Gly Tyr Phe Pro Asp Trp Gln Asn Tyr Thr Pro Gly Pro
            980                 985                 990

Gly Val Arg Tyr Pro Leu Thr Phe Gly Trp Cys Tyr Lys Leu Val Pro
        995                 1000                1005

Val Glu Pro Asp Lys Val Glu Glu Ala Asn Lys Gly Glu Asn Thr Ser
    1010                1015                1020

Leu Leu His Pro Val Ser Leu His Gly Met Asp Asp Pro Glu Arg Glu
1025                1030                1035                1040

Val Leu Glu Trp Arg Phe Asp Ser Arg Leu Ala Phe His His Val Ala
                1045                1050                1055

Arg Glu Leu His Pro Glu Tyr Phe Lys Asn Cys
            1060                1065

```
<210> SEQ ID NO 9
<211> LENGTH: 3411
<212> TYPE: DNA
<213> ORGANISM: Artificial Sequence
<220> FEATURE:
<223> OTHER INFORMATION: p24-RT-Nef-p17 Fusion

<400> SEQUENCE: 9
atggttatcg tgcagaacat ccaggggcaa atggtacatc aggccatatc acctagaact    60
ttaaatgcat gggtaaaagt agtagaagag aaggctttca gcccagaagt aatacccatg   120
ttttcagcat tatcagaagg agccacccca caagatttaa acaccatgct aaacacagtg   180
```

```
gggggacatc aagcagccat gcaaatgtta aaagagacca tcaatgagga agctgcagaa    240
tgggatagag tacatccagt gcatgcaggg cctattgcac caggccagat gagagaacca    300
aggggaagtg acatagcagg aactactagt acccttcagg aacaaatagg atggatgaca    360
aataatccac ctatcccagt aggagaaatt tataaaagat ggataatcct gggattaaat    420
aaaatagtaa gaatgtatag ccctaccagc attctggaca taagacaagg accaaaagaa    480 cctttttagag actatgtaga ccggttctat aaaactctaa gagccgagca agcttcacag    540
gaggtaaaaa attggatgac agaaaccttg ttggtccaaa atgcgaaccc agattgtaag    600
actattttaa aagcattggg accagcggct acactagaag aaatgatgac agcatgtcag    660
ggagtaggag gacccggcca taaggcaaga gttttgcata tgggccccat tagccctatt    720
gagactgtgt cagtaaaatt aaagccagga atggatggcc caaaagttaa acaatggcca    780
ttgacagaag aaaaaataaa agcattagta gaaatttgta cagagatgga aaaggaaggg    840
aaaatttcaa aaattgggcc tgaaaatcca tacaatactc cagtatttgc cataaagaaa    900
aaagacagta ctaaatggag aaaattagta gatttcagag aacttaataa gagaactcaa    960
gacttctggg aagttcaatt aggaatacca catcccgcag ggttaaaaaa gaaaaaatca   1020
gtaacagtac tggatgtggg tgatgcatat ttttcagttc ccttagatga agacttcagg   1080
aaatatactg catttaccat acctagtata aacaatgaga caccagggat tagatatcag   1140
tacaatgtgc ttccacaggg atggaaagga tcaccagcaa tattccaaag tagcatgaca   1200
aaaatcttag agccttttag aaaacaaaat ccagacatag ttatctatca atacatggat   1260
gatttgtatg taggatctga cttagaaata gggcagcata gaacaaaaat agaggagctg   1320
agacaacatc tgttgaggtg gggacttacc acaccagaca aaaaacatca gaaagaacct   1380
ccattcctta aatgggttta tgaactccat cctgataaat ggacagtaca gcctatagtg   1440
ctgccagaaa aagacagctg gactgtcaat gacatacaga agttagtggg gaaattgaat   1500
tgggcaagtc agatttaccc agggattaaa gtaaggcaat tatgtaaact ccttagagga   1560
accaaagcac taacagaagt aataccacta acagaagaag cagagctaga actggcagaa   1620
aacagagaga ttctaaaaga accagtacat ggagtgtatt atgacccatc aaaagactta   1680
atagcagaaa tacagaagca ggggcaaggc caatggacat atcaaattta tcaagagcca   1740
tttaaaaatc tgaaaacagg aaaatatgca agaatgaggg gtgcccacac taatgatgta   1800
aaacaattaa cagaggcagt gcaaaaaata accacagaaa gcatagtaat atggggaaag   1860
actcctaaat ttaaactgcc catacaaaag gaaacatggg aaacatggtg gacagagtat   1920
tggcaagcca cctggattcc tgagtgggag tttgttaata cccctccttt agtgaaatta   1980
tggtaccagt tagagaaaga acccatagta ggagcagaaa ccttctatgt agatggggca   2040
gctaacaggg agactaaatt aggaaaagca ggatatgtta ctaatagagg aagacaaaaa   2100
gttgtcaccc taactgacac aacaaatcag aagactgagt tacaagcaat ttatctagct   2160
ttgcaggatt cgggattaga agtaaacata gtaacagact cacaatatgc attaggaatc   2220
attcaagcac aaccagatca aagtgaatca gagttagtca atcaaataat agagcagtta   2280
ataaaaaagg aaaaggtcta tctggcatgg gtaccagcac acaaaggaat tggaggaaat   2340
gaacaagtag ataaattagt cagtgctgga atcaggaaag tgctagctat gggtggcaag   2400
tggtcaaaaa gtagtgtggt tggatggcct actgtaaggg aaagaatgag acgagctgag   2460
ccagcagcag atggggtggg agcagcatct cgagacctgg aaaaacatgg agcaatcaca   2520
agtagcaata cagcagctac caatgctgct tgtgcctggc tagaagcaca agaggaggag   2580
```

```
gaggtgggtt ttccagtcac acctcaggta cctttaagac caatgactta caaggcagct    2640
gtagatctta gccactttt aaagaaaag ggggactgg aagggctaat tcactcccaa       2700
cgaagacaag atatccttga tctgtggatc taccacacac aaggctactt ccctgattgg    2760
cagaactaca caccagggcc aggggtcaga tatccactga cctttggatg gtgctacaag    2820
ctagtaccag ttgagccaga taaggtagaa gaggccaata aggagagaa caccagcttg     2880 ttacaccctg tgagcctgca tggaatggat gaccctgaga gagaagtgtt agagtggagg    2940
tttgacagcc gcctagcatt tcatcacgtg gcccgagagc tgcatccgga gtacttcaag    3000
aactgcaggc ctatgggtgc gagagcgtca gtattaagcg ggggagaatt agatcgatgg    3060
gaaaaaattc ggttaaggcc agggggaaag aaaaaatata aattaaaaca tatagtatgg    3120
gcaagcagga gctagaacg attcgcagtt aatcctggcc tgttagaaac atcagaaggc     3180
tgtagacaaa tactgggaca gctacaacca tcccttcaga caggatcaga gaacttaga    3240 tcattatata atacagtagc aaccctctat tgtgtgcatc aaaggataga gataaaagac    3300
accaaggaag ctttagacaa gatagaggaa gagcaaaaca aaagtaagaa aaaagcacag    3360
caagcagcag ctgacacagg acacagcaat caggtcagcc aaaattacta a             3411

<210> SEQ ID NO 10
<211> LENGTH: 1136
<212> TYPE: PRT
<213> ORGANISM: Artificial Sequence
<220> FEATURE:
<223> OTHER INFORMATION: p24-RT-Nef-p17 Fusion

<400> SEQUENCE: 10

Met Val Ile Val Gln Asn Ile Gln Gly Gln Met Val His Gln Ala Ile
1               5                   10                  15

Ser Pro Arg Thr Leu Asn Ala Trp Val Lys Val Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Val His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205

Ala Ala Thr Leu Glu Glu Met Met Thr Ala Cys Gln Gly Val Gly Gly
    210                 215                 220
```

-continued

Pro Gly His Lys Ala Arg Val Leu His Met Gly Pro Ile Ser Pro Ile
225                 230                 235                 240

Glu Thr Val Ser Val Lys Leu Lys Pro Gly Met Asp Gly Pro Lys Val
            245                 250                 255

Lys Gln Trp Pro Leu Thr Glu Glu Lys Ile Lys Ala Leu Val Glu Ile
        260                 265                 270

Cys Thr Glu Met Glu Lys Glu Gly Lys Ile Ser Lys Ile Gly Pro Glu
    275                 280                 285

Asn Pro Tyr Asn Thr Pro Val Phe Ala Ile Lys Lys Lys Asp Ser Thr
290                 295                 300

Lys Trp Arg Lys Leu Val Asp Phe Arg Glu Leu Asn Lys Arg Thr Gln
305                 310                 315                 320

Asp Phe Trp Glu Val Gln Leu Gly Ile Pro His Pro Ala Gly Leu Lys
            325                 330                 335

Lys Lys Lys Ser Val Thr Val Leu Asp Val Gly Asp Ala Tyr Phe Ser
        340                 345                 350

Val Pro Leu Asp Glu Asp Phe Arg Lys Tyr Thr Ala Phe Thr Ile Pro
    355                 360                 365

Ser Ile Asn Asn Glu Thr Pro Gly Ile Arg Tyr Gln Tyr Asn Val Leu
370                 375                 380

Pro Gln Gly Trp Lys Gly Ser Pro Ala Ile Phe Gln Ser Ser Met Thr
385                 390                 395                 400

Lys Ile Leu Glu Pro Phe Arg Lys Gln Asn Pro Asp Ile Val Ile Tyr
            405                 410                 415

Gln Tyr Met Asp Asp Leu Tyr Val Gly Ser Asp Leu Glu Ile Gly Gln
        420                 425                 430

His Arg Thr Lys Ile Glu Glu Leu Arg Gln His Leu Leu Arg Trp Gly
    435                 440                 445

Leu Thr Thr Pro Asp Lys Lys His Gln Lys Glu Pro Pro Phe Leu Lys
450                 455                 460

Met Gly Tyr Glu Leu His Pro Asp Lys Trp Thr Val Gln Pro Ile Val
465                 470                 475                 480

Leu Pro Glu Lys Asp Ser Trp Thr Val Asn Asp Ile Gln Lys Leu Val
            485                 490                 495

Gly Lys Leu Asn Trp Ala Ser Gln Ile Tyr Pro Gly Ile Lys Val Arg
        500                 505                 510

Gln Leu Cys Lys Leu Leu Arg Gly Thr Lys Ala Leu Thr Glu Val Ile
    515                 520                 525

Pro Leu Thr Glu Glu Ala Glu Leu Glu Leu Ala Glu Asn Arg Glu Ile
530                 535                 540

Leu Lys Glu Pro Val His Gly Val Tyr Tyr Asp Pro Ser Lys Asp Leu
545                 550                 555                 560

Ile Ala Glu Ile Gln Lys Gln Gly Gln Gly Gln Trp Thr Tyr Gln Ile
            565                 570                 575

Tyr Gln Glu Pro Phe Lys Asn Leu Lys Thr Gly Lys Tyr Ala Arg Met
        580                 585                 590

Arg Gly Ala His Thr Asn Asp Val Lys Gln Leu Thr Glu Ala Val Gln
    595                 600                 605

Lys Ile Thr Thr Glu Ser Ile Val Ile Trp Gly Lys Thr Pro Lys Phe
610                 615                 620

Lys Leu Pro Ile Gln Lys Glu Thr Trp Glu Thr Trp Trp Thr Glu Tyr
625                 630                 635                 640

Trp Gln Ala Thr Trp Ile Pro Glu Trp Glu Phe Val Asn Thr Pro Pro
            645                 650                 655

Leu Val Lys Leu Trp Tyr Gln Leu Glu Lys Glu Pro Ile Val Gly Ala
            660                 665                 670

Glu Thr Phe Tyr Val Asp Gly Ala Ala Asn Arg Glu Thr Lys Leu Gly
            675                 680                 685

Lys Ala Gly Tyr Val Thr Asn Arg Gly Arg Gln Lys Val Val Thr Leu
690                 695                 700

Thr Asp Thr Thr Asn Gln Lys Thr Glu Leu Gln Ala Ile Tyr Leu Ala
705                 710                 715                 720

Leu Gln Asp Ser Gly Leu Glu Val Asn Ile Val Thr Asp Ser Gln Tyr
            725                 730                 735

Ala Leu Gly Ile Ile Gln Ala Gln Pro Asp Gln Ser Glu Ser Glu Leu
            740                 745                 750

Val Asn Gln Ile Ile Glu Gln Leu Ile Lys Lys Glu Lys Val Tyr Leu
            755                 760                 765

Ala Trp Val Pro Ala His Lys Gly Ile Gly Gly Asn Glu Gln Val Asp
            770                 775                 780

Lys Leu Val Ser Ala Gly Ile Arg Lys Val Leu Ala Met Gly Gly Lys
785                 790                 795                 800

Trp Ser Lys Ser Ser Val Val Gly Trp Pro Thr Val Arg Glu Arg Met
            805                 810                 815

Arg Arg Ala Glu Pro Ala Ala Asp Gly Val Gly Ala Ala Ser Arg Asp
            820                 825                 830

Leu Glu Lys His Gly Ala Ile Thr Ser Ser Asn Thr Ala Ala Thr Asn
            835                 840                 845

Ala Ala Cys Ala Trp Leu Glu Ala Gln Glu Glu Glu Val Gly Phe
850                 855                 860

Pro Val Thr Pro Gln Val Pro Leu Arg Pro Met Thr Tyr Lys Ala Ala
865                 870                 875                 880

Val Asp Leu Ser His Phe Leu Lys Glu Lys Gly Gly Leu Glu Gly Leu
            885                 890                 895

Ile His Ser Gln Arg Arg Gln Asp Ile Leu Asp Leu Trp Ile Tyr His
            900                 905                 910

Thr Gln Gly Tyr Phe Pro Asp Trp Gln Asn Tyr Thr Pro Gly Pro Gly
            915                 920                 925

Val Arg Tyr Pro Leu Thr Phe Gly Trp Cys Tyr Lys Leu Val Pro Val
            930                 935                 940

Glu Pro Asp Lys Val Glu Glu Ala Asn Lys Gly Glu Asn Thr Ser Leu
945                 950                 955                 960

Leu His Pro Val Ser Leu His Gly Met Asp Asp Pro Glu Arg Glu Val
            965                 970                 975

Leu Glu Trp Arg Phe Asp Ser Arg Leu Ala Phe His His Val Ala Arg
            980                 985                 990

Glu Leu His Pro Glu Tyr Phe Lys Asn Cys Arg Pro Met Gly Ala Arg
            995                 1000                1005

Ala Ser Val Leu Ser Gly Gly Glu Leu Asp Arg Trp Glu Lys Ile Arg
            1010                1015                1020

Leu Arg Pro Gly Gly Lys Lys Lys Tyr Lys Leu Lys His Ile Val Trp
1025                1030                1035                1040

Ala Ser Arg Glu Leu Glu Arg Phe Ala Val Asn Pro Gly Leu Leu Glu
            1045                1050                1055

Thr Ser Glu Gly Cys Arg Gln Ile Leu Gly Gln Leu Gln Pro Ser Leu
            1060                1065                1070

Gln Thr Gly Ser Glu Glu Leu Arg Ser Leu Tyr Asn Thr Val Ala Thr

```
                      1075                1080                1085
Leu Tyr Cys Val His Gln Arg Ile Glu Ile Lys Asp Thr Lys Glu Ala
            1090                1095                1100
Leu Asp Lys Ile Glu Glu Gln Asn Lys Ser Lys Lys Ala Gln
1105                1110                1115                1120
Gln Ala Ala Ala Asp Thr Gly His Ser Asn Gln Val Ser Gln Asn Tyr
                1125                1130                1135

<210> SEQ ID NO 11
<211> LENGTH: 1554
<212> TYPE: PRT
<213> ORGANISM: Artificial Sequence
<220> FEATURE:
<223> OTHER INFORMATION: Gag-RT-integrase-Nef fusion

<400> SEQUENCE: 11

Met Ala Ala Arg Ala Ser Ile Leu Ser Gly Gly Lys Leu Asp Ala Trp
 1               5                  10                  15
Glu Lys Ile Arg Leu Arg Pro Gly Gly Lys Lys Tyr Arg Leu Lys
             20                  25                  30
His Leu Val Trp Ala Ser Arg Glu Leu Asp Arg Phe Ala Leu Asn Pro
             35                  40                  45
Ser Leu Leu Glu Thr Thr Glu Gly Cys Gln Gln Ile Met Asn Gln Leu
 50                  55                  60
Gln Pro Ala Val Lys Thr Gly Thr Glu Glu Ile Lys Ser Leu Phe Asn
 65                  70                  75                  80
Thr Val Ala Thr Leu Tyr Cys Val His Gln Arg Ile Asp Val Lys Asp
                 85                  90                  95
Thr Lys Glu Ala Leu Asp Lys Ile Glu Glu Ile Gln Asn Lys Ser Lys
            100                 105                 110
Gln Lys Thr Gln Gln Ala Ala Ala Asp Thr Gly Asp Ser Ser Lys Val
        115                 120                 125
Ser Gln Asn Tyr Pro Ile Ile Gln Asn Ala Gln Gly Gln Met Ile His
130                 135                 140
Gln Asn Leu Ser Pro Arg Thr Leu Asn Ala Trp Val Lys Val Ile Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Val Met Leu Asn Ile Val Gly
            180                 185                 190
Gly His Gln Ala Ala Met Gln Met Leu Lys Asp Thr Ile Asn Glu Glu
        195                 200                 205
Ala Ala Glu Trp Asp Arg Leu His Pro Val Gln Ala Gly Pro Ile Pro
    210                 215                 220
Pro Gly Gln Ile Arg Glu Pro Arg Gly Ser Asp Ile Ala Gly Thr Thr
225                 230                 235                 240
Ser Thr Pro Gln Glu Gln Leu Gln Trp Met Thr Gly Asn Pro Pro Ile
                245                 250                 255
Pro Val Gly Asn Ile Tyr Lys Arg Trp Ile Ile Leu Gly Leu Asn Lys
            260                 265                 270
Ile Val Arg Met Tyr Ser Pro Val Ser Ile Leu Asp Ile Lys Gln Gly
        275                 280                 285
Pro Lys Glu Pro Phe Arg Asp Tyr Val Asp Arg Phe Phe Lys Ala Leu
    290                 295                 300
Arg Ala Glu Gln Ala Thr Gln Asp Val Lys Gly Trp Met Thr Glu Thr
305                 310                 315                 320
```

-continued

```
Leu Leu Val Gln Asn Ala Asn Pro Asp Cys Lys Ser Ile Leu Lys Ala
            325                 330                 335
Leu Gly Ser Gly Ala Thr Leu Glu Glu Met Met Thr Ala Cys Gln Gly
        340                 345                 350
Val Gly Gly Pro Gly His Lys Ala Arg Val Leu Ala Glu Ala Met Ser
    355                 360                 365
Gln Ala Gln Gln Thr Asn Ile Met Met Gln Arg Gly Asn Phe Arg Gly
370                 375                 380
Gln Lys Arg Ile Lys Cys Phe Asn Cys Gly Lys Glu Gly His Leu Ala
385                 390                 395                 400
Arg Asn Cys Arg Ala Pro Arg Lys Lys Gly Cys Trp Lys Cys Gly Lys
                405                 410                 415
Glu Gly His Gln Met Lys Asp Cys Thr Glu Arg Gln Ala Asn Phe Leu
            420                 425                 430
Gly Lys Ile Trp Pro Ser Ser Lys Gly Arg Pro Gly Asn Phe Pro Gln
        435                 440                 445
Ser Arg Pro Glu Pro Thr Ala Pro Pro Ala Glu Leu Phe Gly Met Gly
    450                 455                 460
Glu Gly Ile Ala Ser Leu Pro Lys Gln Glu Gln Lys Asp Arg Glu Gln
465                 470                 475                 480
Val Pro Pro Leu Val Ser Leu Lys Ser Leu Phe Gly Asn Asp Pro Leu
                485                 490                 495
Ser Gln Gly Ser Pro Ile Ser Pro Ile Glu Thr Val Pro Val Thr Leu
            500                 505                 510
Lys Pro Gly Met Asp Gly Pro Lys Val Lys Gln Trp Pro Leu Thr Glu
        515                 520                 525
Glu Lys Ile Lys Ala Leu Thr Glu Ile Cys Thr Glu Met Glu Lys Glu
    530                 535                 540
Gly Lys Ile Ser Lys Ile Gly Pro Glu Asn Pro Tyr Asn Thr Pro Ile
545                 550                 555                 560
Phe Ala Ile Lys Lys Lys Asp Ser Thr Lys Trp Arg Lys Leu Val Asp
                565                 570                 575
Phe Arg Glu Leu Asn Lys Arg Thr Gln Asp Phe Trp Glu Val Gln Leu
            580                 585                 590
Gly Ile Pro His Pro Ala Gly Leu Lys Lys Lys Ser Val Thr Val
        595                 600                 605
Leu Asp Val Gly Asp Ala Tyr Phe Ser Val Pro Leu Asp Glu Asn Phe
    610                 615                 620
Arg Lys Tyr Thr Ala Phe Thr Ile Pro Ser Thr Asn Asn Glu Thr Pro
625                 630                 635                 640
Gly Val Arg Tyr Gln Tyr Asn Val Leu Pro Gln Gly Trp Lys Gly Ser
                645                 650                 655
Pro Ala Ile Phe Gln Ser Ser Met Thr Lys Ile Leu Glu Pro Phe Arg
            660                 665                 670
Ser Lys Asn Pro Glu Ile Ile Ile Tyr Gln Tyr Met Ala Ala Leu Tyr
        675                 680                 685
Val Gly Ser Asp Leu Glu Ile Gly Gln His Arg Thr Lys Ile Glu Glu
    690                 695                 700
Leu Arg Ala His Leu Leu Ser Trp Gly Phe Thr Thr Pro Asp Lys Lys
705                 710                 715                 720
His Gln Lys Glu Pro Pro Phe Leu Trp Met Gly Tyr Glu Leu His Pro
                725                 730                 735
Asp Lys Trp Thr Val Gln Pro Ile Met Leu Pro Asp Lys Glu Ser Trp
```

```
                    740                 745                 750
Thr Val Asn Asp Ile Gln Lys Leu Val Gly Lys Leu Asn Trp Ala Ser
            755                 760                 765
Gln Ile Tyr Ala Gly Ile Lys Val Lys Gln Leu Cys Arg Leu Leu Arg
        770                 775                 780
Gly Ala Lys Ala Leu Thr Asp Ile Val Thr Leu Thr Glu Glu Ala Glu
785                 790                 795                 800
Leu Glu Leu Ala Glu Asn Arg Glu Ile Leu Lys Asp Pro Val His Gly
                805                 810                 815
Val Tyr Tyr Asp Pro Ser Lys Asp Leu Val Ala Glu Ile Gln Lys Gln
            820                 825                 830
Gly Gln Asp Gln Trp Thr Tyr Gln Ile Tyr Gln Glu Pro Phe Lys Asn
        835                 840                 845
Leu Lys Thr Gly Lys Tyr Ala Arg Lys Arg Ser Ala His Thr Asn Asp
        850                 855                 860
Val Arg Gln Leu Ala Glu Val Val Gln Lys Val Ala Met Glu Ser Ile
865                 870                 875                 880
Val Ile Trp Gly Lys Thr Pro Lys Phe Lys Leu Pro Ile Gln Lys Glu
                885                 890                 895
Thr Trp Glu Thr Trp Trp Met Asp Tyr Trp Gln Ala Thr Trp Ile Pro
            900                 905                 910
Glu Trp Glu Phe Val Asn Thr Pro Pro Leu Val Lys Leu Trp Tyr Gln
        915                 920                 925
Leu Glu Lys Asp Pro Ile Leu Gly Ala Glu Thr Phe Tyr Val Asp Gly
        930                 935                 940
Ala Ala Asn Arg Glu Thr Lys Leu Gly Lys Ala Gly Tyr Val Thr Asp
945                 950                 955                 960
Arg Gly Arg Gln Lys Val Val Ser Leu Thr Glu Thr Thr Asn Gln Lys
                965                 970                 975
Thr Glu Leu His Ala Ile Leu Leu Ala Leu Gln Asp Ser Gly Ser Glu
            980                 985                 990
Val Asn Ile Val Thr Asp Ser Gln Tyr Ala Leu Gly Ile Ile Gln Ala
        995                 1000                1005
Gln Pro Asp Arg Ser Glu Ser Glu Leu Val Asn Gln Ile Ile Glu Lys
        1010                1015                1020
Leu Ile Gly Lys Asp Lys Ile Tyr Leu Ser Trp Val Pro Ala His Lys
1025                1030                1035                1040
Gly Ile Gly Gly Asn Glu Gln Val Asp Lys Leu Val Ser Ser Gly Ile
                1045                1050                1055
Arg Lys Val Leu Phe Leu Asp Gly Ile Asp Lys Ala Gln Glu Asp His
        1060                1065                1070
Glu Arg Tyr His Ser Asn Trp Arg Thr Met Ala Ser Asp Phe Asn Leu
        1075                1080                1085
Pro Pro Ile Val Ala Lys Glu Ile Val Ala Ser Cys Asp Lys Cys Gln
        1090                1095                1100
Leu Lys Gly Glu Ala Met His Gly Gln Val Asp Cys Ser Pro Gly Ile
1105                1110                1115                1120
Trp Gln Leu Ala Cys Thr His Leu Glu Gly Lys Val Ile Leu Val Ala
                1125                1130                1135
Val His Val Ala Ser Gly Tyr Ile Glu Ala Glu Val Ile Pro Ala Glu
            1140                1145                1150
Thr Gly Gln Glu Thr Ala Tyr Phe Leu Leu Lys Leu Ala Gly Arg Trp
        1155                1160                1165
```

-continued

Pro Val Lys Val Val His Thr Ala Asn Gly Ser Asn Phe Thr Ser Ala
1170                1175                1180

Ala Val Lys Ala Ala Cys Trp Trp Ala Asn Ile Gln Gln Glu Phe Gly
1185                1190                1195                1200

Ile Pro Tyr Asn Pro Gln Ser Gln Gly Val Val Ala Ser Met Asn Lys
        1205                1210                1215

Glu Leu Lys Lys Ile Ile Gly Gln Val Arg Asp Gln Ala Glu His Leu
1220                1225                1230

Lys Thr Ala Val Gln Met Ala Val Phe Ile His Asn Phe Lys Arg Lys
        1235                1240                1245

Gly Gly Ile Gly Gly Tyr Ser Ala Gly Glu Arg Ile Ile Asp Ile Ile
1250                1255                1260

Ala Thr Asp Ile Gln Thr Lys Glu Leu Gln Lys Gln Ile Thr Lys Ile
1265                1270                1275                1280

Gln Asn Phe Arg Val Tyr Tyr Arg Asp Ser Arg Asp Pro Ile Trp Lys
        1285                1290                1295

Gly Pro Ala Lys Leu Leu Trp Lys Gly Glu Gly Ala Val Ile Gln
        1300                1305                1310

Asp Asn Ser Asp Ile Lys Val Val Pro Arg Arg Lys Ala Lys Ile Leu
        1315                1320                1325

Arg Asp Tyr Gly Lys Gln Met Ala Gly Asp Cys Val Ala Gly Arg
        1330                1335                1340

Gln Asp Glu Asp Arg Ser Met Gly Gly Lys Trp Ser Lys Gly Ser Ile
1345                1350                1355                1360

Val Gly Trp Pro Glu Ile Arg Glu Arg Met Arg Arg Ala Pro Ala Ala
        1365                1370                1375

Ala Pro Gly Val Gly Ala Val Ser Gln Asp Leu Asp Lys His Gly Ala
        1380                1385                1390

Ile Thr Ser Ser Asn Ile Asn Asn Pro Ser Cys Val Trp Leu Glu Ala
        1395                1400                1405

Gln Glu Glu Glu Glu Val Gly Phe Pro Val Arg Pro Gln Val Pro Leu
        1410                1415                1420

Arg Pro Met Thr Tyr Lys Gly Ala Phe Asp Leu Ser His Phe Leu Lys
1425                1430                1435                1440

Glu Lys Gly Gly Leu Asp Gly Leu Ile Tyr Ser Arg Lys Arg Gln Glu
        1445                1450                1455

Ile Leu Asp Leu Trp Val Tyr His Thr Gln Gly Tyr Phe Pro Asp Trp
        1460                1465                1470

Gln Asn Tyr Thr Pro Gly Pro Gly Val Arg Tyr Pro Leu Thr Phe Gly
        1475                1480                1485

Trp Cys Phe Lys Leu Val Pro Met Glu Pro Asp Glu Val Glu Lys Ala
        1490                1495                1500

Thr Glu Gly Glu Asn Asn Ser Leu Leu His Pro Ile Cys Gln His Gly
1505                1510                1515                1520

Met Asp Asp Glu Glu Arg Glu Val Leu Ile Trp Lys Phe Asp Ser Arg
        1525                1530                1535

Leu Ala Leu Lys His Arg Ala Gln Glu Leu His Pro Glu Phe Tyr Lys
        1540                1545                1550

Asp Cys

LYOPHILISED ANTIGEN COMPOSITION

CROSS-REFERENCE TO RELATED APPLICATIONS

This application is a divisional of U.S. patent application Ser. No. 12/125,182 filed on May 22, 2008, now abandoned which claims priority to PCT/EP2007/055037 filed May 24, 2007, GB0723044.4 filed Nov. 23, 2007 and GB0723900.7 filed Dec. 6, 2007, all of which are incorporated herein in their entirety.

FIELD OF THE INVENTION

The present invention relates to improved antigenic compositions and methods of using the same to make immunogenic compositions. In particular the present invention relates to lyophilised compositions comprising an antigen and a Toll-like receptor (TLR) 9 agonist. Such compositions may be reconstituted into immunogenic compositions for use in vaccination with a carrier selected from the group of particulate carriers consisting of liposomes, mineral salts, emulsions, polymers and ISCOMs. Methods of making immunogenic compositions from the lyophilised compositions of the invention and use of the same in immunisation are also part of the present invention.

BACKGROUND TO THE INVENTION

Adjuvants are sometimes used to improve the immune response raised to any given antigen. However the inclusion of adjuvants into a vaccine or immunogenic composition increases the complexity of preparation of the components as well as the complexity of distribution and formulation of the vaccine composition. The preparation of each of the adjuvant components as well as the antigenic component must be considered by formulators. This is particularly true because for example the pH of adjuvant components in solution may be very different from the optimal pH for a given antigen and these differences need to be carefully controlled and managed to prevent, for example precipitation or loss of desirable properties of the components. The pH of the antigen in water for injection may, for example be about pH7 or slightly higher and when the adjuvant is added the pH may be as low as pH6.3. The antigen may, for example not be stable when stored for prolonged periods at this pH.

The components must then be formulated and distributed in a form that is as stable as possible because pharmaceutical products for human use must be well characterized, stable and safe before they can be approved for marketing. For this reason long term stability studies must be performed on the final formulation to ensure that it meets the relevant criteria. The information generated in such long term studies is used to support submission to regulatory authorities such as the FDA (Federal Drugs Authority—the body responsible for approving medicines in the USA) to show the product is suitable for use in humans.

Freeze-drying or lyophilisation, is used generally to increase the stability and hence storage life of material including pharmaceutical materials such as an antigen used in vaccines.

Often lyophilised antigenic compositions are provided to health care professions for reconstitution with diluent (for example water for injection [WFI] or in some instances a liquid adjuvant formulation) shortly before administration to the patient. In this way the period of time that the various components of the final vaccine are maintained in close proximity is minimised.

Many factors must be considered when antigens are lyophilised to form lyo cakes (the dry product from lyophilisation). For example, the antigenicity/immunogenicity of the antigen should be maintained in lyophilised form. The antigen must not aggregate or degrade whilst in lyophilised form. The lyo cake must be well formed and not collapse. Finally, the antigen must of course be in a form which dissolves rapidly when reconstituted. Where the solution for reconstitution is not simply WFI, for example when the antigen is reconstituted with liquid adjuvant, then the impact of the components of the solution on the properties of the reconstituted product needs to be considered.

As mentioned adjuvants have been used for many years to improve the immune response to the antigenic component of a vaccine. A particularly potent adjuvant combination is one comprising 3Deacylated-Monophosphoryl Lipid A (3D-MPL) and a saponin, particularly QS21, a purified fraction of saponin extracted from the bark of *Quillaja saponaria* Monara. This combination can be provided, for example as an oil in water emulsion, liposomal formulation or the like.

In previous clinical trials with antigens, for example with malaria antigens such as RTS,S the lyophilized antigen is provided and a separate vial of liquid adjuvant, for example an oil in water formulation of MPL and QS21 or a liposomal formulation of MPL and QS21 for reconstituting the antigen is also provided. The individual components are combined to form the final vaccine composition shortly before administration.

Certain immunostimulatory oligonucleotides containing unmethylated CpG dinucleotides ("CpG") are TLR9 ligands and have been identified as being adjuvants when administered by both systemic and mucosal routes (WO 96/02555, EP 468520, Davis et al., *J. Immunol*, 1998, 160(2):870-876; McCluskie and Davis, *J. Immunol.*, 1998, 161(9):4463-6). CpG is an abbreviation for cytosine-guanosine dinucleotide motifs present in DNA. Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in the present invention.

It has also been shown that an immunostimulatory oligonucleotide can retain immunological activity when the Guanosine is mutated to a 7-deazaguanosine motif (WO 03057822).

These immunostimulatory oligonucleotides are thought to have an acidic pH in solution, for example below pH 7, such as 6.3, 6.1 or lower. This may make them difficult to incorporate in liquid vaccine formulations because they are dissimilar to other components in the formulations. As discussed this may cause precipitation and/or long term stability problems.

It is thought that these immunostimulatory oligonucleotides are likely to be very effective adjuvants, particularly when used in combination with existing adjuvant combinations such as 3D-MPL and QS21. It is expected that such adjuvants will be employed in diseases that have so far been difficult to provide effective vaccines for, such as HIV, cancer and possibly malaria.

There are a number of different ways in which adjuvants can be included in vaccines, but they must be included in a way which does not affect the stability either of themselves or the antigenic composition and also in a way which will not place an undue burden on the healthcare professional reconstituting the vaccine. The simplest way to achieve this would be to put additional components into additional vials such that they would be kept separate until just before reconstitution, thereby minimising the time during which the components could affect each other. This means the antigen and the immunostimulatory oligonucleotide would each be provided in a separate vials. Then if further adjuvant components such as MPL and QS21 are employed these can be provided as a liquid mixture in a third vial. However, an increasing number of components in an increasing number of vials leads to increased costs, waste and importantly to an increase in the possibility of mistakes during constitution.

SUMMARY OF THE INVENTION

The present inventors have found that when a TLR9 ligand such as a CpG immunostimulatory oligonucleotide is to be part of an immunogenic composition as an adjuvant, said TLR9 ligand may be lyophilised together with the antigen such that there is provided a single vial containing antigen and TLR9 ligand adjuvant together in one lyo cake.

The present invention therefore provides a lyophilised composition comprising an antigen and a TLR9 agonist. Said TLR9 agonist in one embodiment is an immunostimulatory oligonucleotide, possibly a CpG containing oligonucleotide. In one aspect, said CpG containing oligonucleotide comprises a Purine, Purine, C,G, pyrimidine, pyrimidine sequence. In another aspect, said immunostimulatory oligonucleotide is selected from the group consisting of: SEQ ID NO:1; SEQ ID NO:2; SEQ ID NO:3; SEQ ID NO:4; and SEQ ID NO:5.

Whilst not wishing to be bound by theory it is thought that providing the antigen and the TLR9 agonist together provides a component that is more stable than simply the addition of the TLR9 to a liquid formulation of MPL and QS21.

The present invention provides the advantage that where the antigen and TLR9 agonist are reconstituted with WFI one is able to provide only one vial with lyophilized formulation in it. Furthermore, where the antigen and the TRL9 agonist are to be reconstituted with a liquid formulation such as a liquid adjuvant formulation then it is advantageous to be able to provide only two vials of components (rather than three). This in turn has cost benefits, whilst providing a product suitable for use a vaccine once reconstituted.

Furthermore, the present inventors have found that the co-lyophilisation of CpG with antigens which would not have an overall positive charge in the reconstitution buffer may increase the solubility of those antigens on reconstitution with either water for injection or liquid adjuvant. Therefore the present invention also provides a method to increase the solubility of a lyophilised antigen on reconstitution where the antigen would not have a net positive charge in the reconstitution buffer comprising the step of co-lyophilising a TLR9 agonist, preferably an immunostimulatory oligonucleotide and more preferably a CpG oligonucleotide with the antigen.

The present invention also provides for the use of a TLR9 agonist, preferably an immunostimulatory oligonucleotide and more preferably a CpG oligonucleotide to increase the solubility of a lyophilised non-positively charged antigen on reconstitution. By "non-positively charged" is meant that the overall charge of the protein is not positive. The protein may contain both positive and negative charges, but the overall charge of the protein is either neutral or negative.

The present invention also provides a method of making an immunogenic composition comprising the steps of reconstituting a lyophilised composition as described herein with a suitable carrier. In one embodiment, said carrier is a liposomal solution or an oil in water emulsion. Said carrier may optionally contain one or more immunostimulants, which may be selected from the group consisting of TLR4 agonists, TLR4 antagonists, saponins, TLR7 agonists, TLR8 agonists, TLR9 agonists. In one embodiment, said carrier contains two or more immunostimulants and in one aspect these may be 3-deacylated MPL and QS21.

The present invention also provides a method of making a lyophilised composition of the invention comprising combining one or more desired antigens, a TLR9 ligand and suitable excipients and freeze drying the resulting mixture.

BRIEF DESCRIPTION OF THE DRAWINGS

FIG. 5: A representation of the antigen used in example 2: a portion of the protein D protein linked to MAGE-3, which in turn was linked to a His tail for ease of purification PD-Mage3-His

DETAILED DESCRIPTION OF THE INVENTION

Figure 1:
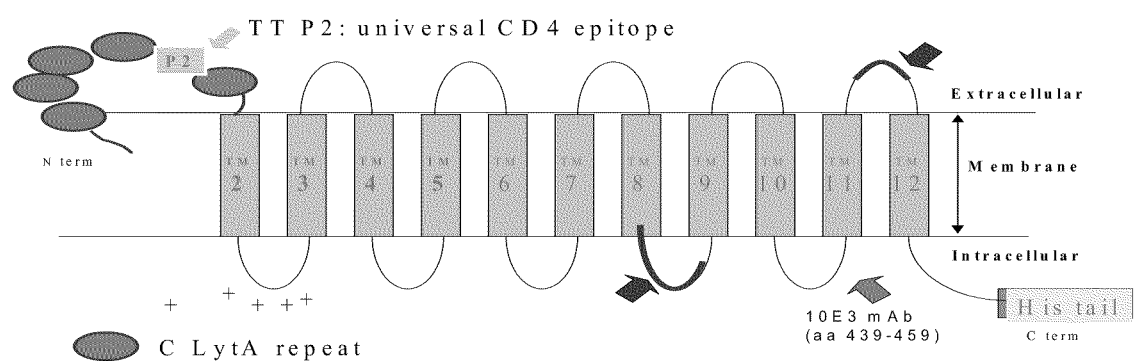
FIG. 1: A diagrammatic representation of CPC-P501S

The present inventors have found that TLR9 ligands such a CpG oligonucleotides may be lyophilised with an antigen of interest without affecting the antigenicity or stability of that antigen. By TLR9 ligand is meant a compound that can interact with the TLR9 receptor. Members of the Toll-Like Receptor (TLR) family, first discovered in *Drosophila*, have been shown to be pattern recognition receptors, each member recognizing and responding to different microbial components to limit/eradicate invading microbes. Binding of pathogen-associated molecular patterns (PAMP) to TLRs induces the production of reactive oxygen and nitrogen intermediates, initiation of the pro-inflammatory cytokine network, and upregulation of costimulatory molecules linking the rapid innate response to the adaptive immunity. Many TLR ligands are known to be useful as adjuvants. TLR9 has been shown to respond to oligonucleotide agonists. Therefore the TLR9 ligands of the invention are immunostimulatory oligonucleotides. In one embodiment of the invention, such TLR9 ligands contain a CpG motif. Alternative immunostimulatory oligonucleotides may comprise modifications to the nucleotides. For example, WO0226757 and WO03057822 disclose modifications to the C and G portion of a CpG containing immunostimulatory oligonucleotides.

In one embodiment, the TLR9 ligands are CpG oligonucleotides. In one aspect of this embodiment, a CpG oligonucleotide contains two or more dinucleotide CpG motifs separated by at least three, possibly at least six or more nucleotides. The oligonucleotides of the present invention are typically deoxynucleotides. In one embodiment the internucleotide bond in the oligonucleotide is phosphorodithioate, or possibly a phosphorothioate bond, although phosphodiester and other internucleotide bonds could also be used, including oligonucleotides with mixed internucleotide linkages. Methods for producing phosphorothioate oligonucleotides or phosphorodithioate are described in U.S. Pat. Nos. 5,666,153, 5,278,302 and WO95/26204. Oligonucleotide comprising different internucleotide linkages are contemplated, e.g. mixed phosphorothioate phophodiesters. Other internucleotide bonds which stabilise the oligonucleotide may be used.

Examples of CpG oligonucleotides have the following sequences. In one embodiment, these sequences contain phosphorothioate modified internucleotide linkages.

```
OLIGO 1 (SEQ ID NO: 1):
TCC ATG ACG TTC CTG ACG TT (CpG 1826)

OLIGO 2 (SEQ ID NO: 2):
TCT CCC AGC GTG CGC CAT (CpG 1758)

OLIGO 3 (SEQ ID NO: 3):
ACC GAT GAC GTC GCC GGT GAC GGC ACC ACG

OLIGO 4 (SEQ ID NO: 4):
TCG TCG TTT TGT CGT TTT GTC GTT (CpG 2006)

OLIGO 5 (SEQ ID NO: 5):
TCC ATG ACG TTC CTG ATG CT (CpG 1668)
```

Alternative CpG oligonucleotides may comprise the sequences above in that they have inconsequential deletions or additions thereto.

The CpG oligonucleotides utilised in the present invention may be synthesized by any method known in the art (eg EP 468520). Conveniently, such oligonucleotides may be synthesized utilising an automated synthesizer.

In the context of the present specification, the term "antigen" is intended to refer to an immunogenic component suitable for raising a specific immune response and suitable for inclusion into to a vaccine or immunogenic composition, for example an antigen for inclusion in a HIV-1 vaccine, a cancer vaccine, a malaria vaccine, a TB vaccine or the like. Details of specific antigens are given below.

In one embodiment the antigen has an isoelectric point of 9.6 or less. In one embodiment the antigen has isoelectric point of 9 or less. In one embodiment the antigen has an isoelectric point of 8.5 or less. In one embodiment the antigen has an isoelectric point of 8.0 or less. In one embodiment the antigen has an isoelectric point of 7.5. In one embodiment the antigen has an isoelectric point in the range 7 to 8.

The net charge of a protein when reconstituted in buffer depends on the number of positive versus the number of negative charges in the protein, this charge will of course vary depending on the pH of the reconstitution buffer Isoelectric point is the pH at which the net charge of a protein is neutral. If the pH of the reconstitution buffer is below the isoelectric point of the antigen, the protein tends to carry a net positive charge. If the pH of the reconstitution buffer is above the isoelectric point of the antigen, the protein tends to carry a net negative charge. The present invention is particularly useful when lyophilising and reconstituting antigens which have an isoelectric point such that, in the intended reconstitution buffer, the protein would carry a net negative charge. In such circumstances (see example 3), the presence of CpG in the lyophilised composition can enhance solubility of the antigen in the reconstitution buffer.

In one embodiment the lyophilized antigen and TLR9 agonist is provided as one dose, for example in one vial.

In one embodiment the lyphilized antigen is present in an amount to provide an antigen concentration in the range of 10 to 250 µg, when reconstituted.

In one embodiment the TRL9 agonist is present in an amount to provide a concentration in the range of 10 to 1000 µg such as 500 µg, when reconstituted.

In one embodiment of the invention, the antigen which is combined in a lyophilised composition with a TLR9 ligand may be an anti-tumour antigen. Therefore immunogenic compositions made using the lyophilised antigenic composition of the invention are useful for the immunotherapeutic treatment of cancers. For example, lyophilised composition may be prepared with cancer antigens, tumour antigens or tumour rejection antigens as described herein, such as those proteins expressed in prostate cancer, breast cancer, colorectal cancers, lung cancer, kidney cancer, ovarian cancer, liver cancer and head and neck cancer, among others.

Cancer testis antigens that may be used in the present invention include the MAGE A family of antigens MAGE-A1, A2, A3, A4, A5, A6, A7, A8, A9, A10, A11 and A12; also known as MAGE-1, 2, 3, 4, 5, 6, 7, 8, 9, 10, 11, 12), the MAGE B antigens MAGE B1, B2, B3 and B4, the MAGE C antigens MAGE-C1 and MAGE-C2, the LAGE 1 antigen, the LAGE 2 antigen (also known as NY-ESO-1) and the GAGE antigen.

Prostate specific antigens may also be used in the present invention. Examples of prostate specific antigens that may be fused include six-transmembrane epithelial antigen of the prostate (STEAP), Prostate Specific Antigen (PSA), prostatic acid phosphatase (PAP), prostate stem cell antigen (PSCA), prostate-specific membrane antigen (PSMA) or the antigen known as prostase (also known as P703P).

In one embodiment, the prostate antigen is P501S or a fragment thereof. P501S, also named protein, is a 553 amino acid protein. Immunogenic fragments and portions of P501S comprising at least 20, 50, or 100 contiguous amino acids, or fragments comprising between 20-50 or 50-100 contiguous amino acids, may be used as the tumour associated antigen or derivative of the present invention. In one embodiment the tumour associated antigen or derivative is the PS108 antigen (disclosed in WO98/50567) or prostate cancer-associated protein (see WO99/67384). In some embodiments, fragments are amino acids 51-553, 34-553 or 55-553 of the full-length P501S protein. These can be expressed in yeast systems, for example DNA sequences encoding such polypeptides can be expressed in yeast systems.

In one embodiment, the antigen may comprise or consist of WT-1 expressed by the Wilm's tumor gene, or its N-terminal fragment WT-1F comprising about or approximately amino acids 1-249. WT1 is a protein originally found to be overexpressed in paediatric kidney cancer, Wilm's Tumor. An antigen that may be used comprises nearly the full length protein as antigen. In one embodiment, the antigen may comprise or consist of the WT1-A10 protein, which is a 292 AA recombinant fusion protein consisting of a 12mer truncated tat sequence and amino acids number 2-281 of the WT1 sequence.

In one embodiment of the invention the tumour associated antigen or derivative is a breast cancer antigen, for example Her-2/neu, mammaglobin or a B305D antigen.

The Her-2/neu antigen for use in the present invention may comprises the entire extracellular domain (ECD; for example the sequence comprising approximately amino acid 1-645 of the amino acid sequence of Her-2/neu) or fragments thereof. Alternatively or additionally the construct may comprise at least an immunogenic portion of or the entire intracellular domain: for example approximately the C terminal 580 amino acids of the Her-2/neu sequence.

One construct that may be used as the tumour associated antigen derivative of the present invention is a fusion protein of the ECD and the phosphorylation domain (PD) of Her-2/neu (ECD-PD). A further construct that may be used is a fusion protein of the ECD and a fragment of the phosphorylation domain of Her-2/neu (ECD-ΔPD). The Her-2/neu fusion proteins and constructs as described may be derived from human, rat, mouse or simian/monkey Her-2/neu. Exemplary sequences and constructs of Her-2/neu are described in WO00/44899.

PRAME (also known as DAGE) is another antigen that may be used as the tumour associated antigen of the present invention. Fusion proteins as described herein that comprise the PRAME antigen may also be used. In particular, fusions of the PRAME antigen as described herein and a protein D fusion partner protein or derivative as described herein are contemplated for use in the present invention.

PRAME antigen has been shown by some groups to be expressed in melanoma and a wide variety of tumours including lung, kidney and head and neck cancer. Interestingly it also seems to be expressed in 40-60% leukemia such as acute lymphoid leukemia and acute myeloid leukemia, see for example Exp Hematol. 2000 December; 28(12):1413-22. In patients it has been observed that over expression of PRAME seems to be associated with higher survival and lower rates of relapse in comparison to those who do not over express the protein.

The antigen and its preparation are described in U.S. Pat. No. 5,830,753. PRAME is found in the Annotated Human Gene Database H-Inv DB under the accession numbers: U65011.1, BC022008.1, AK129783.1, BC014974.2, CR608334.1, AF025440.1, CR591755.1, BC039731.1, CR623010.1, CR611321.1, CR618501.1, CR604772.1, CR456549.1, and CR620272.1.

In one aspect the antigen of the present invention may comprise or consist of a PRAME antigen or immunogenic fragment thereof. Generally the PRAME protein has 509 amino acids and in one embodiment all 509 amino acids of PRAME may be included in the antigen.

Colorectal antigens may also be used as the tumour associated antigens of the present invention. Examples of colorectal antigens that could be used include: C1585P (MMP 11) and C1491 (E1A Enhancer Binding Protein), CASB618 (as described in WO00/53748); CASB7439 (as described in WO01/62778); and C1584 (Cripto).

Other tumour associated antigens useful in the context of the present invention include: Plu-1 J. Biol. Chem. 274 (22) 15633-15645, 1999, HASH-1, HASH-2, Cripto (Salomon et al Bioessays 199, 21 61-70, U.S. Pat. No. 5,654,140) Criptin U.S. Pat. No. 5,981,215. Additionally, antigens particularly relevant for vaccines in the therapy of cancer also comprise tyrosinase and survivin.

Mucin derived peptides such as Muc1 see for example U.S. Pat. No. 5,744,144 U.S. Pat. No. 5,827,666 WO 8805054, U.S. Pat. No. 4,963,484. Specifically contemplated are Muc 1 derived peptides that comprise at least one repeat unit of the Muc 1 peptide, preferably at least two such repeats and which is recognised by the SM3 antibody (U.S. Pat. No. 6,054,438). Other mucin derived peptides include peptide from Muc 5.

Other tumour-specific antigens are suitable for use in the lyophillised composition of the present invention and include, but are not restricted to tumour-specific gangliosides such as GM 2, and GM3 or conjugates thereof to carrier proteins; or said antigen may be a self peptide hormone such as whole length Gonadotrophin hormone releasing hormone (GnRH, WO 95/20600), a short 10 amino acid long peptide, useful in the treatment of many cancers, or in immunocastration.

The invention also extends to use of the above antigens, immunogenic derivatives and immunogenic fragments and fusion proteins comprising same in aspects of the present invention.

Derivatives, Fragments and Fusion Proteins

Tumour associated antigens of the present invention may be employed in the form of derivatives or fragments thereof rather than the naturally-occurring antigen.

As used herein the term "derivative" refers to an antigen that is modified relative to its naturally occurring form. The derivative may include a mutation, for example a point mutation. In one example, the derivative may change the properties of the protein, for example by improving expression in prokaryotic systems or by removing undesirable activity, e.g., enzymatic activity. Derivatives of the present invention are sufficiently similar to native antigens to retain antigenic properties and remain capable of allowing an immune response to be raised against the native antigen. Whether or not a given derivative raises such an immune response may be measured by a suitably immunological assay such as an ELISA or flow cytometry.

In one embodiment of the present invention the derivative of the tumour associated antigen of the present invention is a fusion protein comprising a tumour associated antigen linked to a heterologous fusion partner protein. By "heterologous" with respect to a tumour associated antigen is intended a protein or polypeptide sequence that would not be linked to the tumour associated antigen in nature, i.e., is linked to the tumour associated antigen by deliberate human intervention.

The antigen and heterologous fusion partner protein may be chemically conjugated or may be expressed as recombinant fusion proteins. In one embodiment, a fusion protein of the present invention may allow increased levels of the fusion protein to be produced in an expression system compared to non-fused protein. Thus the fusion partner protein may assist in providing T helper epitopes, for example T helper epitopes recognised by humans (ie. the fusion partner protein is acting as an immunological fusion partner). The fusion partner may assist in expressing the protein at higher yields than the native recombinant protein (i.e., the fusion partner protein acting as an expression enhancer). In one embodiment, the fusion partner protein may act as both an immunological fusion partner and expression enhancing partner.

Fusion partner proteins may, for example, be derived from protein D. Protein D is a lipoprotein (a 42 kDa immunoglobulin D binding protein exposed on the surface of the Gram-negative bacterium *Haemophilus influenzae*). The protein is synthesized as a precursor with an 18 amino acid residue signal sequence, containing a consensus sequence for bacterial lipoprotein (see WO 91/18926). Native precursor Protein D protein is processed during secretion and the signal sequence is cleaved. The Cys of the processed Protein D (at position 19 in the precursor molecule) becomes the N terminal residue of the processed protein and is concomitantly modified by covalent attachment of both ester-linked and amide-linked fatty acids. The fatty acids linked to the amino-terminal Cysteine residue then function as membrane anchor.

In one embodiment, the tumour associated antigen derivative for use in the present invention may comprise Protein D or a derivative thereof as a fusion partner protein.

The protein D or a derivative thereof as described herein may comprise, for example: the first or N-terminal third of processed protein D or approximately or about the first or N-terminal third of processed protein D. In one embodiment, the protein D or a derivative thereof may comprise the first or N-terminal 100 to 115 amino acids of processed protein D; or the first or N-terminal 109 amino acids of processed protein D. In one embodiment, the native processed Protein D amino acids 2-Lys and 2-Leu may be substituted with amino acids 2-Asp and 3-Pro.

In one embodiment, the protein D or derivative thereof may further include the 18 or 19 amino acid signal sequence of precursor protein D. In one embodiment, the fusion partner protein derived from protein D comprises or consists of amino acids 20 to 127 of precursor protein D. In one embodiment of the present invention, the two amino acids 21-Lys and 22-Leu of the precursor protein D fusion partner protein may be substituted with amino acids 21-Asp and 22-Pro.

The protein D fusion partner protein as described herein may additionally or alternatively contain deletions, substitutions or insertions within the amino acid sequence when compared to the wild-type precursor or processed protein D sequence. In one embodiment, 1, 2, 3, 4, 5, 6, 7, 8, 9 or more amino acids may be inserted, substituted or deleted. The amino acids may be substituted with conservative substitutions as defined herein, or other amino acids may be used.

In one embodiment, the fusion partner protein may comprise or consist of a protein D sequence as shown in SEQ ID NO: 1. In one embodiment, the fusion partner protein may comprise or consist of the amino acids underlined in FIG. 1, ie., amino acid residues 20 through 127 of SEQ ID NO: 12. In one embodiment, the antigen for use in the present invention may be protein-D-MAGE-3, in which the MAGE-3 antigen consists of amino acids 3 to 314 of MAGE-3 and in which the protein D fusion partner protein consists of the amino acid sequence shown in FIG. 1.

In another embodiment of the present invention, fusion partner proteins may be selected from NS1 or LytA or derivatives thereof as described below.

NS1 is a non-structural protein from the influenzae virus. In one embodiment, the tumour associated antigen derivative of the present invention may comprise NS1 or a derivative thereof as a fusion partner protein. The NS1 or derivative thereof may comprise the N terminal 1 to 81 amino acids thereof.

LytA is derived from *Streptococcus pneumoniae*. The C-terminal domain of the LytA protein is responsible for the affinity to the choline or to some choline analogues such as DEAE. In one embodiment, the tumour associated antigen derivative of the present invention may comprise LytA or a derivative thereof as a fusion partner protein. The LytA or derivative thereof may comprise the repeat portion of the LytA molecule found in the C terminal end starting at residue 178. In one embodiment, the LytA or derivative thereof comprises residues 188-305 of C-LytA.

Immunogenic polypeptides for use in the present invention will typically be recombinant proteins produced, e.g., by expression in a heterologous host such as a bacterial host, in yeast or in cultured mammalian cells.

The term "tumor associated antigen derivative" means a polypeptide which partially or wholly contains sequences which occur naturally in a tumor associated antigen or which bears a high degree of sequence identity thereto (e.g., more than 95% identity over a stretch of at least 10, e.g., at least 20 amino acids). Derivatives also include sequences having conservative substitutions. Conservative substitutions are well known and are generally set up as the default scoring matrices in sequence alignment computer programs.

In general terms, substitution within the following groups are conservative substitutions, but substitutions between the following groups are considered non-conserved. The groups are:
i) Aspartate/asparagine/glutamate/glutamine
ii) Serine/threonine
iii) Lysine/arginine
iv) Phenylalanine/tyrosine/tryptophane
v) Leucine/isoleucine/valine/methionine
vi) Glycine/alanine Derivatives of the present invention may also include chemically treated sequences such as treatment with an aldehyde (such as formaldehyde or glutaraldehyde), carboxymethylation, carboxyamidation, acetylation and other routine chemical treatments. Constructs of the present invention having derivatised free thiol residues may also be used in the present invention. In particular carboxyamidated or carboxymethylated thiol derivatives may be used.

In one embodiment of the present invention the tumor associated antigen derivative may be a MAGE antigen as described herein having derivatised free thiol residues. The derivatised free thiol residues may be a carboxyamide or carboxymethylated derivatives.

The tumour associated antigen derivative of the present invention may alternatively comprise a construct comprising more than one tumour associated antigen. In one embodiment of the present invention, the tumour associated antigen derivative may comprise two or more tumour associated antigens.

The term "fragment" as used herein refers to fragments of a tumour associated antigen or derivative of the antigen which contain at least one epitope, for example a CTL epitope, typically a peptide of at least 8 amino acids. Fragments of at least 8, for example 8-10 amino acids or up to 20, 50, 60, 70, 100, 150 or 200 amino acids in length are considered to fall within the scope of the invention as long as the fragment demonstrates antigenicity, that is to say that the major epitopes (e.g., CTL epitopes) are retained by the fragment and the fragment is capable of inducing an immune response that cross-reacts with the naturally occurring tumour associated antigen. Exemplary fragments may be 8-10, 10-20, 20-50, 50-60, 60-70, 70-100, 100-150, 150-200 amino acid residues in length (inclusive of any value within these ranges).

In one embodiment of the invention, the lyophilised composition comprising Her 2 neu antigen and CpG oligonucleotide is reconstituted with a liposome or oil in water emulsion carrier containing 3D-MPL and QS21. Such reconstituted formulations produce both a humoral and cellular mediated response.

The lyophilised compositions of the invention may contain antigens associated with tumour-support mechanisms (e.g. angiogenesis, tumour invasion) for example tie 2, VEGF.

In another aspect of the invention, the antigen within the lyophilised composition of the invention is an antigen selected from HIV derived antigens, particularly HIV-1 derived antigens. The following passages describe the antigens which may be derived from HIV-1.

HIV Tat and Nef proteins are early proteins, that is, they are expressed early in infection and in the absence of structural protein.

The Nef gene encodes an early accessory HIV protein which has been shown to possess several activities. For example, the Nef protein is known to cause the removal of CD4, the HIV receptor, from the cell surface, although the biological importance of this function is debated. Additionally Nef interacts with the signal pathway of T cells and induces an active state, which in turn may promote more efficient gene expression. Some HIV isolates have mutations or deletions in this region, which cause them not to encode functional protein and are severely compromised in their replication and pathogenesis in vivo.

The Gag gene is translated from the full-length RNA to yield a precursor polyprotein which is subsequently cleaved into 3-5 capsid proteins; the matrix protein p17, capsid protein p24 and nucleic acid binding protein (Fundamental Virology, Fields B N, Knipe D M and Howley M 1996 2. Fields Virology vol 2 1996).

The Gag gene gives rise to the 55-kilodalton (Kd) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the Pol gene) during the process of viral maturation into four smaller proteins designated MA (matrix [p17]), CA (capsid [p24]), NC (nucleocapsid [p9]), and p6.

In addition to the 3 major Gag proteins (p17, p24 and p9), all Gag precursors contain several other regions, which are cleaved out and remain in the virion as peptides of various sizes. These proteins have different roles e.g. the p2 protein has a proposed role in regulating activity of the protease and contributes to the correct timing of proteolytic processing.

The MA polypeptide is derived from the N-terminal, myristoylated end of p55. Most MA molecules remain attached to the inner surface of the virion lipid bilayer, stabilizing the particle. A subset of MA is recruited inside the deeper layers of the virion where it becomes part of the complex which escorts the viral DNA to the nucleus. These MA molecules facilitate the nuclear transport of the viral genome because a karyophilic signal on MA is recognized by the cellular nuclear import machinery. This phenomenon allows HIV to infect non-dividing cells, an unusual property for a retrovirus.

The p24 (CA) protein forms the conical core of viral particles. Cyclophilin A has been demonstrated to interact with the p24 region of p55 leading to its incorporation into HIV particles. The interaction between Gag and cyclophilin A is essential because the disruption of this interaction by cyclosporine inhibits viral replication.

The NC region of Gag is responsible for specifically recognizing the so-called packaging signal of HIV. The packaging signal consists of four stem loop structures located near the 5' end of the viral RNA, and is sufficient to mediate the incorporation of a heterologous RNA into HIV-1 virions. NC binds to the packaging signal through interactions mediated by two zinc-finger motifs. NC also facilitates reverse transcription.

The p6 polypeptide region mediates interactions between p55 Gag and the accessory protein Vpr, leading to the incorporation of Vpr into assembling virions. The p6 region also contains a so-called late domain which is required for the efficient release of budding virions from an infected cell.

The Pol gene encodes three proteins having the activities needed by the virus in early infection, reverse transcriptase RT, protease, and the integrase protein needed for integration of viral DNA into cellular DNA. The primary product of Pol is cleaved by the virion protease to yield the amino terminal RT peptide which contains activities necessary for DNA synthesis (RNA and DNA directed DNA polymerase, ribonuclease H) and carboxy terminal integrase protein. HIV RT is a heterodimer of full-length RT (p66) and a cleavage product (p51) lacking the carboxy terminal RNase H domain.

RT is one of the most highly conserved proteins encoded by the retroviral genome. Two major activities of RT are the DNA Pol and ribonuclease H. The DNA Pol activity of RT uses RNA and DNA as templates interchangeably and like all DNA polymerases known is unable to initiate DNA synthesis de novo, but requires a pre existing molecule to serve as a primer (RNA).

The RNase H activity inherent in all RT proteins plays the essential role early in replication of removing the RNA genome as DNA synthesis proceeds. It selectively degrades the RNA from all RNA-DNA hybrid molecules. Structurally the polymerase and ribo H occupy separate, non-overlapping domains within the Pol covering the amino two thirds of the Pol.

The p66 catalytic subunit is folded into 5 distinct subdomains. The amino terminal 23 of these have the portion with RT activity. Carboxy terminal to these is the RNase H domain.

After infection of the host cell, the retroviral RNA genome is copied into linear double stranded DNA by the reverse transcriptase that is present in the infecting particle. The integrase (reviewed in Skalka A M '99 Adv in Virus Res 52 271-273) recognises the ends of the viral DNA, trims them and accompanies the viral DNA to a host chromosomal site to catalyse integration. Many sites in the host DNA can be targets for integration. Although the integrase is sufficient to catalyse integration in vitro, it is not the only protein associated with the viral DNA in vivo—the large protein—viral DNA complex isolated from the infected cells has been denoted the pre integration complex. This facilitates the acquisition of the host cell genes by progeny viral genomes.

The integrase is made up of 3 distinct domains, the N terminal domain, the catalytic core and the C terminal domain. The catalytic core domain contains all of the requirements for the chemistry of polynucleotidyl transfer.

HIV-1 derived antigens for use in the invention may thus for example be selected from Gag (for example full length Gag), p17 (a portion of Gag), p24 (another portion of Gag), p41, p40, Pol (for example full length Pol), RT (a portion of Pol), p51 (a portion of RT), integrase (a portion of Pol), protease (a portion of Pol), Env, gp120, gp140 or gp160, gp41, Nef, Vif, Vpr, Vpu, Rev, Tat and immunogenic derivatives thereof and immunogenic fragments thereof, particularly Env, Gag, Nef and Pol and immunogenic derivatives thereof and immunogenic fragments thereof including p17, p24, RT and integrase. HIV vaccines may comprise polypeptides and/or polynucleotides encoding polypeptides corresponding to multiple different HIV antigens for example 2 or 3 or 4 or more HIV antigens which may be selected from the above list. Several different antigens may, for example, be comprised in a single fusion protein. More than one first immunogenic polypeptide and/or more than one second immunogenic polypeptide each of which is an HIV antigen or a fusion of more than one antigen may be employed.

For example an antigen may comprise Gag or an immunogenic derivative or immunogenic fragment thereof, fused to RT or an immunogenic derivative or immunogenic fragment thereof, fused to Nef or an immunogenic derivative or immunogenic fragment thereof wherein the Gag portion of the fusion protein is present at the 5' terminus end of the polypeptide.

A Gag sequence of use according to the invention may exclude the Gag p6 polypeptide encoding sequence. A particular example of a Gag sequence for use in the invention comprises p17 and/or p24 encoding sequences.

A RT sequence may contain a mutation to substantially inactivate any reverse transcriptase activity (see WO03/025003).

The RT gene is a component of the bigger pol gene in the HIV genome. It will be understood that the RT sequence employed according to the invention may be present in the context of Pol, or a fragment of Pol corresponding at least to RT. Such fragments of Pol retain major CTL epitopes of Pol. In one specific example, RT is included as just the p51 or just the p66 fragment of RT.

The RT component of the fusion protein or composition according to the invention optionally comprises a mutation to remove a site which serves as an internal initiation site in prokaryotic expression systems.

Optionally the Nef sequence for use in the invention is truncated to remove the sequence encoding the N terminal region i.e. removal of from 30 to 85 amino acids, for example from 60 to 85 amino acids, particularly the N terminal 65 amino acids (the latter truncation is referred to herein as trNef). Alternatively or additionally the Nef may be modified to remove the myristylation site. For example the Gly 2 myristylation site may be removed by deletion or substitution. Alternatively or additionally the Nef may be modified to alter the dileucine motif of Leu 174 and Leu 175 by deletion or substitution of one or both leucines. The importance of the dileucine motif in CD4 downregulation is described e.g. in Bresnahan P. A. et al (1998) Current Biology, 8(22): 1235-8.

The Env antigen may be present in its full length as gp160 or truncated as gp140 or shorter (optionally with a suitable mutation to destroy the cleavage site motif between gp120 and gp41). The Env antigen may also be present in its naturally occurring processed form as gp120 and gp41. These two derivatives of gp160 may be used individually or together as a combination. The aforementioned Env antigens may further exhibit deletions (in particular of variable loops) and truncations. Fragments of Env may be used as well.

An exemplary gp120 sequence is shown in SEQ ID No 6. An exemplary gp140 sequence is shown in SEQ ID No 7.

Immunogenic polypeptides for use in a lyophilised composition according to the invention may comprise Gag, Pol, Env and Nef wherein at least 75%, or at least 90% or at least 95%, for example, 96% of the CTL epitopes of these native antigens are present.

In lyophilised compositions comprising immunogenic polypeptides which comprise p17/p24 Gag, p66 RT, and truncated Nef as defined above, 96% of the CTL epitopes of the native Gag, Pol and Nef antigens are suitably present.

One embodiment of the invention provides a lyophilised composition comprising a TLR9 ligand and an immunogenic polypeptide containing p17, p24 Gag, p66 RT, truncated Nef (devoid of nucleotides encoding terminal amino-acids 1-85-"trNef") in the order Gag, RT, Nef.

Specific polynucleotide constructs and corresponding polypeptide antigens for use in lyophilised compositions according to the invention include:

1. p17, p24 (codon optimised) Gag-p66 RT (codon optimised)-truncated Nef;
2. truncated Nef-p66 RT (codon optimised)-p17, p24 (codon optimised) Gag;
3. truncated Nef-p17, p24 (codon optimised) Gag-p66 RT (codon optimised);
4. p66 RT (codon optimised)-p17, p24 (codon optimised) Gag-truncated Nef;
5. p66 RT (codon optimised)-truncated Nef-p17, p24 (codon optimised) Gag;
6. p17, p24 (codon optimised) Gag-truncated Nef-p66 RT (codon optimised).

An exemplary fusion is a fusion of Gag, RT and Nef particularly in the order Gag-RT-Nef (see eg SEQ ID No 8 or SEQ ID NO: 9) Another exemplary fusion is a fusion of p17, p24, RT and Nef particularly in the order p24-RT-Nef-p17. This fusion is called F4 and is described in WO2006/013106. F4 is a preferred example of an HIV antigen which may be found in a lyophilised composition of the invention. The nucleotide sequence of F4 is given in SEQ ID NO:10 where p24 sequence is in bold, the Nef sequence is underlined, and the boxes are nucleotides introduced by genetic construction. The amino acid sequence of F4 is given in SEQ ID NO:11, where:

P24 sequence: amino-acids 1-232 (in bold)
RT sequence: amino-acids 235-795
Nef sequence: amino-acids 798-1002
P17 sequence: amino-acids 1005-1136
Boxes: amino-acids introduced by genetic construction
K (Lysine): instead of Tryptophan (W). Mutation introduced to remover enzyme activity In another embodiment a lyophilised composition contains Gag, RT, integrase and Nef, especially in the order Gag-RT-integrase-Nef (see eg SEQ ID No 11).

In other embodiments the HIV antigen may be a fusion polypeptide which comprises Nef or an immunogenic derivative thereof or an immunogenic fragment thereof, and p17 Gag and/or p24 Gag or immunogenic derivatives thereof or immunogenic fragments thereof, wherein when both p17 and p24 Gag are present there is at least one HIV antigen or immunogenic fragment between them.

For example, Nef is suitably full length Nef.

For example p17 Gag and p24 Gag are suitably full length p17 and p24 respectively.

In one embodiment a lyophilised composition contains an immunogenic polypeptide comprising both p17 and p24 Gag or immunogenic fragments thereof. In such a construct the p24 Gag component and p17 Gag component are separated by at least one further HIV antigen or immunogenic fragment, such as Nef and/or RT or immunogenic derivatives thereof or immunogenic fragments thereof. See WO2006/013106 for further details.

In fusion proteins which comprise p24 and RT, it may be preferable that the p24 precedes the RT in the construct because when the antigens are expressed alone in *E. coli* better expression of p24 than of RT is observed.

Some constructs for use in lyophilised compositions according to the invention include the following:

1. p24-RT-Nef-p17
2. p24-RT*-Nef-p17
3. p24-p51RT-Nef-p17
4. p24-p51 RT*-Nef-p17
5. p17-p51RT-Nef
6. p17-p51RT*-Nef
7. Nef-p17
8. Nef-p17 with linker
9. p17-Nef
10. p17-Nef with linker * represents RT methionine$_{592}$ mutation to lysine In another aspect the present invention provides a lyophilised composition containing a fusion protein of HIV antigens comprising at least four HIV antigens or immunogenic fragments, wherein the four antigens or fragments are or are derived from Nef, Pol and Gag. Preferably Gag is present as two separate components which are separated by at least one other antigen in the fusion. Preferably the Nef is full length Nef. Preferably the Pol is p66 or p51RT. Preferably the Gag is p17 and p24 Gag. Other preferred features and properties of the antigen components of the fusion in this aspect of the invention are as described herein.

Preferred embodiments of this aspect of the invention are the four component fusions as already listed above:
1. p24-RT-Nef-p17
2. p24-RT*-Nef-p17
3. p24-p51RT-Nef-p17
4. p24-p51RT*-Nef-p17

The immunogenic polypeptides used within the lyophilised composition of the present invention may have linker sequences present in between the sequences corresponding to particular antigens such as Gag, RT and Nef. Such linker sequences may be, for example, up to 20 amino acids in length. In a particular example they may be from 1 to 10 amino acids, or from 1 to 6 amino acids, for example 4-6 amino acids.

Further description of such suitable HIV antigens can be found in WO03/025003.

HIV antigens for use in the present invention may be derived from any HIV clade, for example clade A, clade B or clade C. For example the HIV antigens may be derived from clade A or B, especially B.

In one specific embodiment of the invention, a lyophilised composition contains more than one immunogenic polypeptide. In one aspect of this embodiment a first immunogenic polypeptide is a polypeptide comprising Gag and/or Pol and/or Nef or a fragment or derivative of any of them (eg p24-RT-Nef-p17). In one specific aspect of this embodiment of the invention a second immunogenic polypeptide is a polypeptide comprising Gap and/or Pol and/or Nef or a fragment or derivative of any of them (eg Gag-RT-Nef or Gag-RT-integrase-Nef).

Thus in one specific embodiment, a polypeptide comprising Gap and/or Pol and/or Nef or a fragment or derivative of any of them (eg p24-RT-Nef-p17) is a first immunogenic polypeptide and a polypeptide comprising Gap and/or Pol and/or Nef or a fragment or derivative of any of them (eg Gag-RT-Nef or Gag-RT-integrase-Nef) is a second immunogenic polypeptide.

In another specific embodiment of the invention, a first immunogenic polypeptide is Env or a fragment or derivative thereof eg gp120, gp140 or gp160 (especially gp120). In one specific embodiment of the invention a second immunogenic polypeptide is a polypeptide comprising Gag and/or Pol and/or Nef or a fragment or derivative of any of them (eg p24-RT-Nef-p17).

Thus in one specific embodiment, Env or a fragment or derivative thereof eg gp120, gp140 or gp160 (especially gp120) is a first immunogenic polypeptide and a polypeptide comprising Gag and/or Pol and/or Nef or a fragment or derivative of any of them (eg p24-RT-Nef-p17) is a second immunogenic polypeptide.

In another specific embodiment of the invention, a first immunogenic polypeptide is a polypeptide comprising Gag and/or Pol and/or Nef or a fragment or derivative of any of them (eg p24-RT-Nef-p17). In one specific embodiment of the invention a second immunogenic polypeptide is Env or a fragment or derivative thereof eg gp120, gp140 or gp160 (especially gp120).

Thus in one specific embodiment, a polypeptide comprising Gag and/or Pol and/or Nef or a fragment or derivative of any of them (eg p24-RT-Nef-p17) is a first immunogenic polypeptide and Env or a fragment or derivative thereof eg gp120, gp140 or gp160 (especially gp120) is a second immunogenic polypeptide.

The lyophilised composition may contain one antigen, or may contain more than one antigen.

In one aspect of the invention, the TLR9 ligand is used to improve the solubility of non-positively charged antigens. The present inventors have found that, particularly with antigens which are negatively charged, the co-lyophilisation of Cpg can improve their solubility on reconstitution. Where the TLR9 ligand is an immunostimulatory oligonucleotide, the antigen will be a molecule with a net negative charge. Where this ligand is co-lyophilised with an antigen with a net positive charge, there is a possibility that the TLR9 ligand will interact with the antigen upon reconstitution of the lyophilised composition, possibly causing precipitation of the antigen. This is not desirable, but can be avoided by one of skill in the art by including with the composition for lyophilisation excipients which are known to increase solubility in such situations such as, for example, L-arginine.

The TLR9 ligand and one or more antigens are combined with suitable excipients to form the final bulk formulation which will be lyophilised. Optimally, the excipients will contain a cryoprotectant to protect the protein from denaturation during the early stages of lyophilisation, and a lyoprotectant to prevent protein inactivation during drying. Two different molecules may be used, or one molecule may be used that has both properties, such as a disaccharide. Optionally, a crystalline bulking agent such as mannitol or glycine may also be added. A non-ionic surfactant such as polysorbate or Tween® may also be added to help prevent aggregation of the protein. Excipients could also include buffer salts to modify the pH of the final bulk.

Suitable excipients include the following: sugars such as sucrose, trehalose, raffinose and maltodextrins such as maltotriose, maltotetraose, maltopentaose or maltohexaose; polyols such as mannitol or sorbitol; polymers such as dextran, polyethylene glycol (PEG), or polyvinylpyrrolidone (PVP); amino acids such as glycine, alanine or arginine.

Excipients may also be combined such that two or more, for example three or four excipients may be used together. Possible combinations include sugar and dextran, for example sucrose and dextran or trehalose and dextran; sugar and PEG, for example PEG8000 and saccharides; sugar and PVP for example sucrose and PVP; sugar and amino acids, for example glycine and sucrose; two sugars together, for example sucrose and glucose or sucrose and raffinose; sucrose and polyols, for example sucrose and sorbitol or sucrose and mannitol; polyols and amino acids, such as mannitol and glycine.

Surfactants such as polysorbate or Tween® may be added to any combination of excipients.

In order to form an immunogenic composition which can be used for vaccination, the lyophilised composition containing the antigen and the TLR9 ligand is reconstituted with a pharmaceutically acceptable diluent. It is a preferred aspect of the invention that such diluent should be a particulate diluent, for example a solution of metal salt particles, or liposomes, or an oil in water emulsion.

In one embodiment, the diluent contains further immunostimulants. This means that the final reconstituted immunogenic composition will contain other immunostimulants in addition to the TLR9 ligand found in the lyophilised composition.

There are a number of known immunostimulants which are known to be adjuvants either alone or in combination. The innate or natural immune system recognises a wide spectrum of pathogens without a need for prior exposure. The main cells responsible for innate immunity, monocytes/macrophages and neutrophils, phagocytose microbial pathogens and trigger the innate, inflammatory, and specific immune responses.

Lipopolysaccharides (LPS) are the major surface molecule of, and occur exclusively in, the external leaflet of the outer membrane of gram-negative bacteria. LPS have been shown to be TLR4 ligands. LPS impede destruction of bacteria by serum complements and phagocytic cells, and are involved in adherence for colonisation. LPS are a group of structurally related complex molecules of approximately 10,000 Daltons in size and consist of three covalently linked regions:
  (i) an O-specific polysaccharide chain (O-antigen) at the outer region
  (ii) a core oligosaccharide central region
  (iii) lipid A—the innermost region which serves as the hydrophobic anchor, it comprises glucosamine disaccharide units which carry long chain fatty acids.

The biological activities of LPS, such as lethal toxicity, pyrogenicity and adjuvanticity, have been shown to be related to the lipid A moiety. In contrast, immunogenicity is associated with the O-specific polysaccharide component (O-antigen). Both LPS and lipid A have long been known for their strong adjuvant effects, but the high toxicity of these molecules has precluded their use in vaccine formulations. Significant effort has therefore been made towards reducing the toxicity of LPS or lipid A while maintaining their adjuvanticity.

The *Salmonella minnesota* mutant R595 was isolated in 1966 from a culture of the parent (smooth) strain (Luderitz et al. 1966 *Ann. N.Y. Acad. Sci.* 133:349-374). The colonies selected were screened for their susceptibility to lysis by a panel of phages, and only those colonies that displayed a narrow range of sensitivity (susceptible to one or two phages only) were selected for further study. This effort led to the isolation of a deep rough mutant strain which is defective in LPS biosynthesis and referred to as *S. minnesota* R595.

In comparison to other LPS, those produced by the mutant *S. minnesota* R595 have a relatively simple structure.
  (i) they contain no O-specific region—a characteristic which is responsible for the shift from the wild type smooth phenotype to the mutant rough phenotype and results in a loss of virulence
  (ii) the core region is very short—this characteristic increases the strain susceptibility to a variety of chemicals
  (iii) the lipid A moiety is highly acylated with up to 7 fatty acids.

4'-monophosphoryl lipid A (MPL), which may be obtained by the acid hydrolysis of LPS extracted from a deep rough mutant strain of gram-negative bacteria, retains the adjuvant properties of LPS while demonstrating a toxicity which is reduced by a factor of more than 1000 (as measured by lethal dose in chick embryo eggs) (Johnson et al. 1987 *Rev. Infect. Dis.* 9 Suppl:S512-S516). LPS is typically refluxed in mineral acid solutions of moderate strength (e.g. 0.1 M HCl) for a period of approximately 30 minutes. This process results in dephosphorylation at the 1 position, and decarbohydration at the 6' position, yielding MPL.

3-O-deacylated monophosphoryl lipid A (3D-MPL), which may be obtained by mild alkaline hydrolysis of MPL, has a further reduced toxicity while again maintaining adjuvanticity, see U.S. Pat. No. 4,912,094 (Ribi Immunochemicals). Alkaline hydrolysis is typically performed in organic solvent, such as a mixture of chloroform/methanol, by saturation with an aqueous solution of weak base, such as 0.5 M sodium carbonate at pH 10.5.

Further information on the preparation of 3D-MPL is available in, for example, U.S. Pat. No. 4,912,094 and WO02/078637 (Corixa Corporation).

Some molecules which are not TLR ligands have been shown to have adjuvant activity. Quillaja saponins are a mixture of triterpene glycosides extracted from the bark of the tree *Quillaja saponaria*. Crude saponins have been extensively employed as veterinary adjuvants. Quil-A is a partially purified aqueous extract of the Quillaja saponin material. QS21 is a Hplc purified non toxic fraction of Quil A and its method of its production is disclosed (as QA21) in U.S. Pat. No. 5,057,540.

In one aspect of the invention, the diluent contains one further immunostimulant. In another aspect of the invention, the diluent contains more than one further immunostimulant. Such immunostimulants may be TLR4 ligands, saponins, TLR7 ligands, TLR8 ligands or TLR9 ligands. In one embodiment of the invention, the further immunostimulant is a TLR4 ligand such as 3D-MPL as described herein. In a further embodiment of the invention, the further immunostimulant is QS21 as described herein. In yet a further embodiment of the invention, the diluent contains QS21 and 3D-MPL. In one aspect of this embodiment, the diluent is an oil in water emulsion containing QS21 and 3D-MPL. In another aspect of this embodiment, the diluent is a solution of liposomes containing QS21 and 3D-MPL.

The invention will now be described further by way of reference to the following, non-limiting examples.

EXAMPLES

Example 1

Freeze Drying of a CpG Oligonucleotide and Cpc-P501S as Antigen

The antigen used was CPC-P501S. This antigen is shown in FIG. 1 diagrammatically, in which the section showing TM2 to TM12 represents the P501S antigen; the oval shapes on the left hand side represent the CPC fusion partners and the His tail is shown on the right hand side.

The antigen was produced with a His tag as shown in *S. cerevisiae* and then made to a concentration of 700 μg/ml using a buffer of Tris (5 mM pH7.5) and Tween80 (0.3%).

To prepare the final bulk, sucrose (35%) was added to water for injection to reach a final concentration of 6.3%. Tris (1M pH8.8) was then added, followed by Tween 80 (25%) to reach a final concentration of 0.2%. This mixture was magnetically stirred for 5 minutes at room temperature. CPC-P501S was added and the mixture was magnetically stirred for 4 minutes at room temperature. A CpG oligo of SEQ ID No:4 was then added, and the resulting mixture magnetically stirred for 15 minutes at room temperature to give the final bulk. The composition was analysed as follows:

|  | Final Bulk (500 μl) | Final container (500 μl) Human dose |  | Final Bulk (500 μl) | Final container (500 μl) Human dose |
|---|---|---|---|---|---|
| Cakes |  | After reconstitution with 625 μl AS01B | Cakes |  | After reconstitution with 625 μl AS01B |
| CPC-P501 | 125 μg | 100 μg | CPC-P501 | 25 μg | 20 μg |
| CpG | 625 μg | 500 μg | CpG | 625 μg | 500 μg |
| Tris | 50 mM | 40 mM | Tris | 50 mM | 40 mM |
| Tween 80 | 0.50% | 0.40% | Tween 80 | 0.20% | 0.16% |
| Saccharose | 6.3% | 5.0% | Saccharose | 6.3% | 5.0% |
| pH | 9.1 +/− 0.1 | 7.4 +/− 0.1 | pH | 9.1 +/− 0.1 | 7.4 +/− 0.1 |

Figure 2:
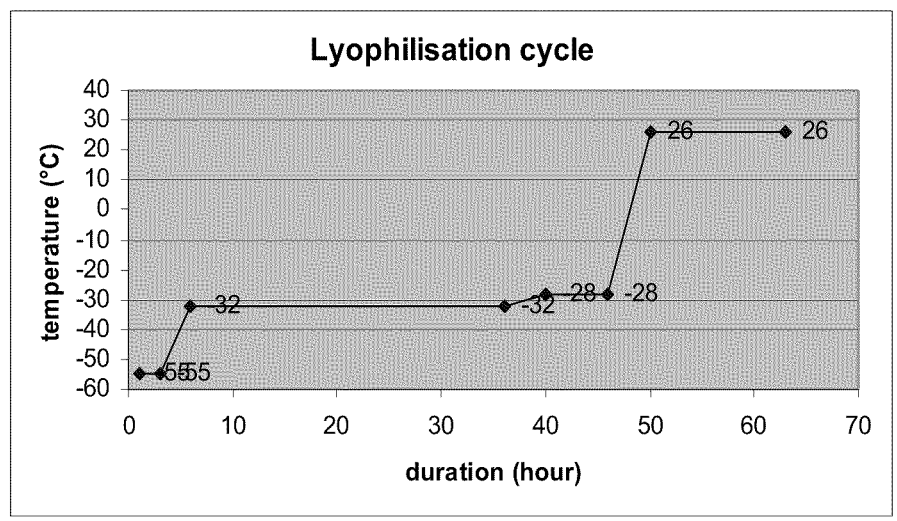
FIG. 2: The lyophillisation cycle used for CpG-P501S

0.5 ml of a composition was filled into a glass vial, which was put through the lyophilisation cycle as shown in FIG. 2.

Figure 3:
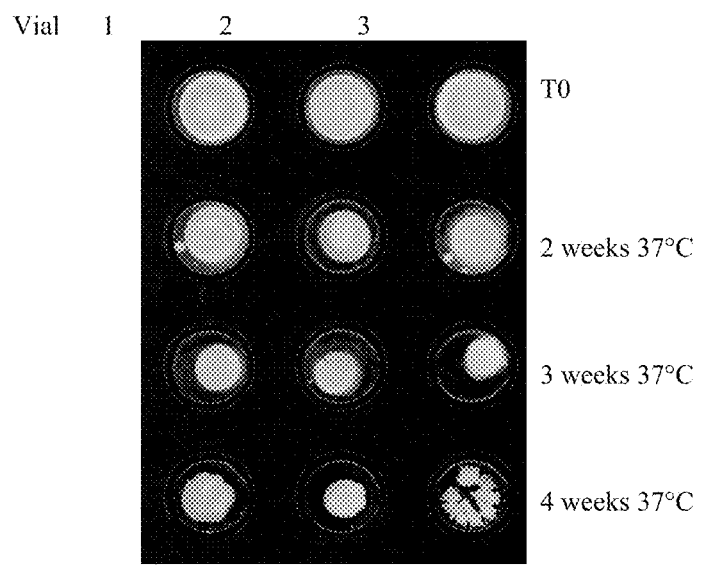
FIG. 3: Visual inspection of three vials of the lyophilised composition

Cake characterisation was carried out by visual inspection and diameter measurement at T0, 1 week, 2 weeks, 3 weeks, and 4 weeks at 37° C., on three vials of the composition (see FIG. 3). Residual humidity content was measured at the same timepoints and temperature using thermogravimetry (TG) or Karl Fischer (KF). As can be seen below, the cakes were stable for up to two weeks.

| Stability timing | Freeze-dried cake | | Moisture content (% wH$_2$O/w cake) | |
|---|---|---|---|---|
| | Visual aspect | Cake diameter (mm) | KF | TG |
| T0 | OK | 12.6 ± 0.1 | 0.3% (1.5 month at 4° C.) | 0.8% (5 month at 4° C.) |
| 1 week 37° C. | OK | nd | 0.59% | nd |
| 2 week 37° C. | Retraction+ | 9.8 ± 0.8 | nd | 1.4% |
| 3 week 37° C. | Retraction++ | 7.7 ± 1.0 | nd | 1.2% |
| 4 week 37° C. | Retraction++ | 8.7 ± 1.5 | Not measurable | 1.3% |

KF: Karl Fischer method
TG: Thermogravimetry method
nd: not done
OK: neither aggregation nor degradation
Specs: 3% (Thermogravimetry)

The humidity in a final container stored at 37° C. (to accelerate stability analysis) increases during time. After 1 month at 37° C., cakes contain 1.3% H2O and are retracted. In this experiment, the increase in humidity is due to the fact that hygroscopic powder absorbs water from the stoppers. Replacing the stoppers with new types of stoppers can help prevent this retraction.

The cakes were then reconstituted either with water for injection, or with the following carrier liquids: Adjuvant system A (a liposomal adjuvant prepared as set out in WO2005/112991), Adjuvant system E (an oil in water emulsion adjuvant prepared as set out in WO2005/112991) or adjuvant system F (an oil in water emulsion adjuvant prepared as set out in WO2005/112991).

No protein aggregation or degradation was seen with water for injection, adjuvant system E or adjuvant system F. Some aggregation and degradation was seen with adjuvant system A. It was concluded that this was due to the decrease of the pH below the isoelectric point of CPC-P501S. An increase in the concentration of the Tris excipient to 50 mM solved the problem and no aggregation was then seen with adjuvant system A. It was also found that the presence of CpG in the lyo cake (i.e. co-lyophilisation of antigen and CpG oligonucleotide) helped prevent aggregation of the antigen when reconstituted with adjuvant system A. A comparison of reconstitution of lyo cakes with and without CpG using adjuvant system A showed that there was reduced aggregation following co-lyophilisation (data not shown)

Figure 4:
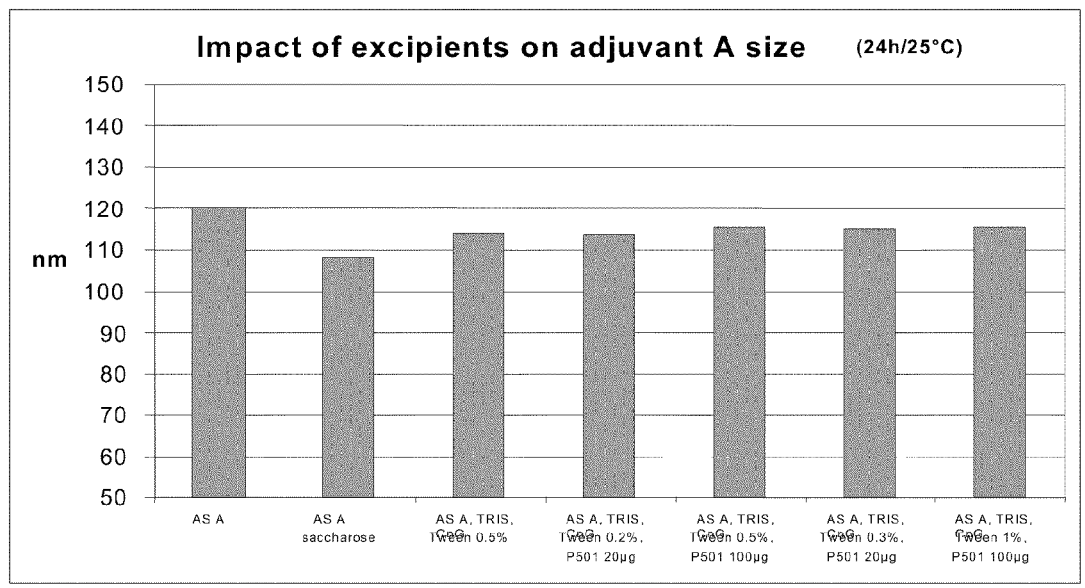
FIG. 4: An analysis of the impact of lyophilisation on the particle size of adjuvant A

The impact of the excipients of the size of the liposomes in adjuvant system A was also studied, and it was found that there was no difference in size between liposomes found in a vial of adjuvant system A alone and liposomes found in a vial of adjuvant system A after reconstitution of a lyo-cake containing antigen, CpG, Tris and Tween. Therefore we can conclude that the components of the lyo-cake do not affect the adjuvant system (FIG. 4)

Finally, the antigenicity of the formulation was studied, and it was found that in terms of lymphoproliferation and intracellular cytokine (IFNγ) production, there was no difference between a liquid versus a lyo formulation of CPC-P501S (data not shown). Therefore we can conclude that the immunogenicity of the antigen is unaffected by co-lyophilisation with CpG.

Example 2

Freeze Drying of a CpG Oligonucleotide and Mage-3 as Antigen

The antigen used was a portion of the protein D protein linked to MAGE-3, which in turn was linked to a His tail for ease of purification PD-Mage3-His (see FIG. 5: SEQ ID NO: 13).

The purified bulk antigen was produced with a His tag in *E. coli* and then made to a concentration of 750 μg/ml using a buffer of $NaH_2PO_4.2H_2O/K_2HPO_4.2H_2O$ (2 mM) and Tween80 at approximately 0.2% v/v (theoreitical) pH7.5.

To prepare the final bulk, sucrose (30%) was added to water for injection to give a final concentration of 3.15%. $NaH_2PO_4.2H_2O/K_2HPO_4.2H_2O$ (100 mM pH7.5) was then added to give a final $PO_4$ concentration of 5 mM taking into account the phosphate found in the antigen buffer. Tween 80 (3%) was also added to give a final concentration of 0.15%, taking into account the Tween found in the antigen buffer. This mixture was magnetically stirred for between 5 and 15 minutes at room temperature. PD-Mage3-His was added (750 μg/ml) and the mixture was magnetically stirred for 5-15 minutes at room temperature. A CpG oligo of Seq ID No:4 was then added, and the resulting mixture magnetically stirred for 15 minutes (+/−5 minutes) at room temperature to give the final bulk. The pH was adjusted to pH7.5+/−0.1 with NaOH 0.05 M or 0.5 M, or HCl 0.03 M or 0.3 M.

The composition was analysed as follows:

Residual humidity of cakes stored for between 7 to 9 days at 37° C. stays below the specification of 3%.

There was no evolution in the diameter following storage for between 7 to 9 days at 37° C.

The cakes were then reconstituted with Adjuvant system A (a liposomal adjuvant prepared as set out in WO2005/112991). No protein aggregation or degradation was seen, thereby confirming that the antigen can be co-lyophilised with CpG without affecting its ability to be reconstituted.

Figure 7:
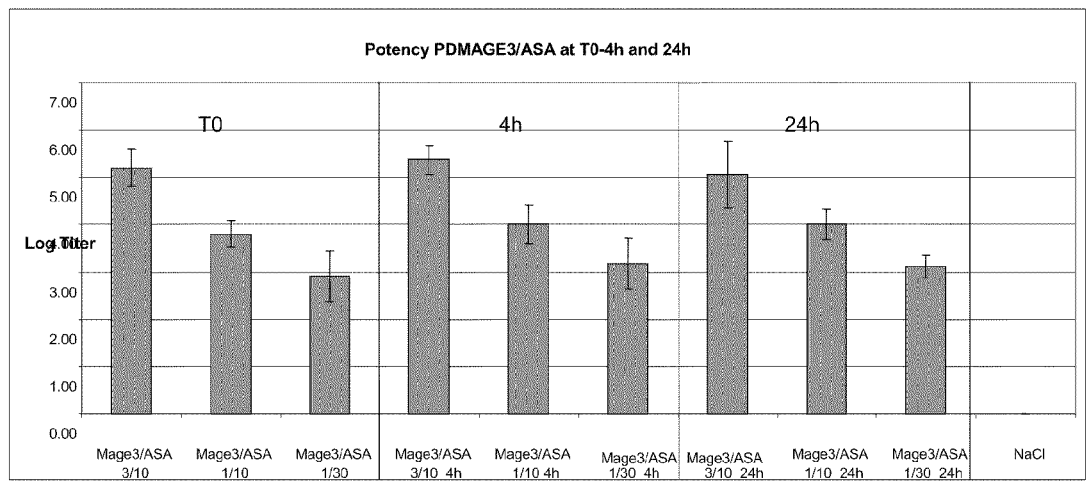
FIG. 7: In-vivo potency results test for lyophilised CpG-Mage3 formulations

The antigenicity of the formulation was studied. It was found that, following reconstitution in Adjuvant system A, there was a decrease in antigenicity with time, after 24 hours. It is thought that this is due to the acidic pH (6.2+/−0.1) found following reconstitution. This was confirmed when it was found that the antigenicity fall could be decreased by increasing the pH. However there was still some decrease in antigenicity over time. Therefore the formulations were tested to see if this decrease had an effect on the in-vivo potency test. Dilutions of ³⁄₁₀, ¹⁄₁₀ and ¹⁄₃₀$^{th}$ of a human dose were given to groups of mice, 10 mice per group as shown in FIG. 7. Mice were bled at day 28.

T0, 4 h and 24 h are the times following reconstitution of the cake with adjuvant system A. As can be seen in FIG. 7, there was no effect on potency.

Example 3

Impact of CpG on Antigen Solubility Following Reconstitution

1. WT1 is a protein originally found to be overexpressed in paediatric kidney cancer, Wilm's Tumor. The candidate antigen used in the present case uses nearly the full length protein

| | Ingredients | | | Before freeze-drying | | Per HD (after reconstit. with 0.625 ml of diluent) | |
|---|---|---|---|---|---|---|---|
| | | | | | Weight | | Weight |
| N° | Name | Component | Src | CC | (in 0.5 ml) | Concentrat | (in 0.5 ml) |
| 1 | PD-Mage3-His | NaH2PO4.2H2O—K2HPO4.3H2O 2 mM/Tween 80 ~0.2% v/v theo pH 7.5 | | 750 μg/ml | 375 μg | 600 μg/ml | 300 μg |
| 2 | CpG | | | 1250 μg/ml | 625 μg | 1000 μg/ml | 500 μg |
| 3 | saccharose | | | 3.15% w/v | 15.75 mg | 2.52% w/v | 12.6 mg |
| 4 | Tween 80 | | 1 | 0.15% w/v | | 0.12% w/v | |
| 5 | PO4 | | 1 | 5 mM | | 4 mM | |
| 6 | WFI | | | | ad 0.5 ml | | |
| 7 | pH | | | | 7.5 +/− 0.1 | | |

Figure 6:
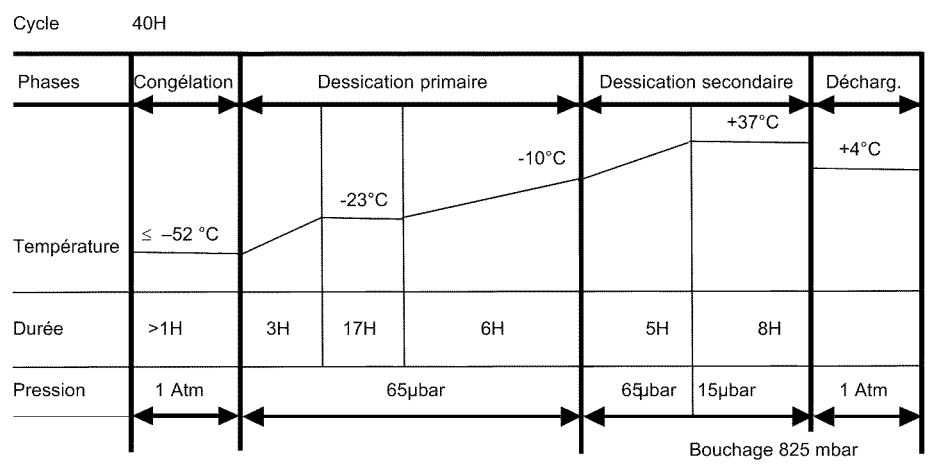
FIG. 6: The lyophillisation cycle used for CpG-Mage3

0.5 ml of this composition was filled into a glass vial, which was put through the lyophilisation cycle shown in FIG. 6.

The Impact of excipients and freeze-drying cycle on cake composition was analysed after between 7 to 9 days of cake storage at 37° C.

| cake aspect and residual humidity | | |
|---|---|---|
| Cake aspect | No collapse (T0) | No retraction (T7d 37° C.) |
| Residual humidity | — | 0.59% (T8d 37° C.) |

It can be seen that the cakes do not present any collapse at 7 days and do not change through 8 days of stress stability.

as antigen. The WT1-A10 protein is a 292 AA recombinant fusion protein expressed in *E. coli* consisting of a 12 mer truncated tat sequence (leader sequence) and amino acids number 2-281 of the WT1 sequence. After lyophilisation alone, this antigen precipitates if reconstituted with adjuvant system A due to its isoelectric point (5.85 to 7.5) which is close to the pH of adjuvant system A (6.1) and the presence of sodium chloride in adjuvant system A.

Two formulations of WT1-A10 were prepared. The reconstituted dose contained 400 μg/ml of WT1-A10 antigen, 10% sucrose, 100 mM Tris, and 0.2% Tween 80, plus or minus 840 μg/ml CpG.

Both formulations were reconstituted with 500 μl of adjuvant system A. The resulting liquid was centrifuged and a Western blot performed on the non-centrifuged liquid (NC), the supernatant (SN) and the pellet (P). The results are shown in FIG. 8.

Figure 8:
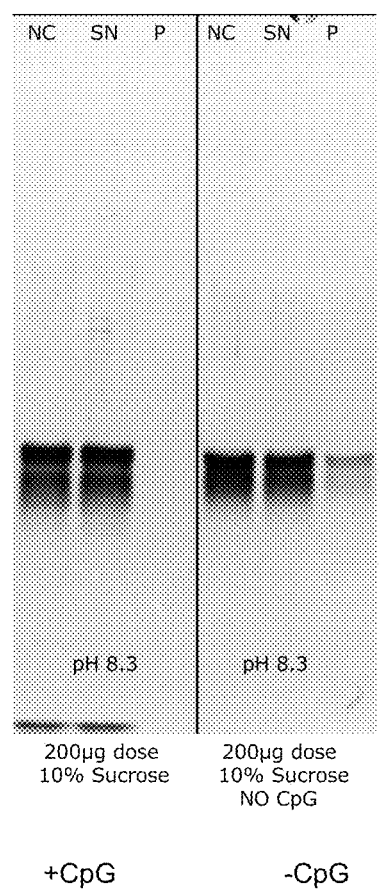
FIG. 8: Impact of CpG on antigen solubility following reconstitution (WT-1)

As can be seen in FIG. 8, in the presence of CpG, the solubility of the antigen after reconstitution is improved as evidenced by the lack of antigen in the precipitate pellet. Precipitated antigen can be seen in the pellet of the reconstituted lyophilised composition where the lyo cake did not contain CpG. This is evidence that, in the case of a non-positively charged antigen, the co-lyophilisation of CpG improves the solubility of the antigen on reconstitution.

2. PRAME

Two formulations of PRAME were prepared. The reconstituted dose contained 1000 µg/ml of PRAME antigen, 3.15% sucrose, 5 mM Borate, 150 nM Sodium Chloride, plus or minus 840 µg/ml CpG. Both formulations were reconstituted with 500 µl of adjuvant system A.

Figure 9:
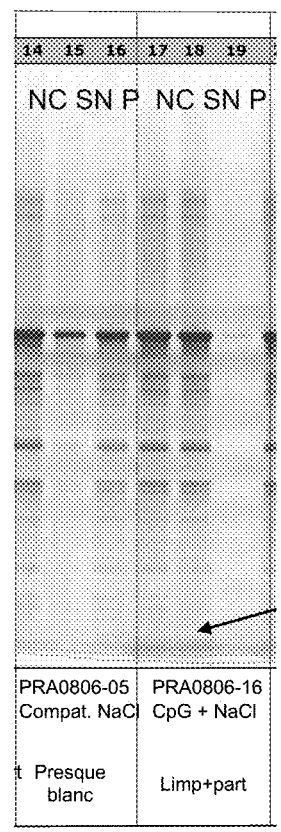
FIG. 9: Impact of CpG on antigen solubility following reconstitution (PRAME)

The resulting liquid was centrifuged and a Western blot performed on the non-centrifuged liquid (NC), the supernatant (SN) and the pellet (P). The results are shown in FIG. 9, where NC=non-centrifuged, SN=supernatant and P=pellet As can be seen in FIG. 9, in the presence of CpG, the solubility of the antigen after reconstitution is improved as evidenced by the lack of antigen in the precipitate pellet. Precipitated antigen can be seen in the pellet of the reconstituted lyophilised composition where the lyo cake did not contain CpG. This is further evidence that, in the case of a non-positively charged antigen, the co-lyophilisation of CpG improves the solubility of the antigen on reconstitution.

```
                                                                     SEQ ID NO: 1
         TCC ATG ACG TTC CTG ACG TT
                                                                     SEQ ID NO: 2
         TCT CCC AGC GTG CGC CAT
                                                                     SEQ ID NO: 3
         ACC GAT GAC GTC GCC GGT GAC GGC ACC ACG
                                                                     SEQ ID NO: 4
         TCG TCG TTT TGT CGT TTT GTC GTT
                                                                     SEQ ID NO: 5
         TCC ATG ACG TTC CTG ATG CT

SEQ ID NO: 6
         MKVKETRKNY QHLWRWGTML LGMLMICSAA EQLWVTVYYG VPVWKEATTT    50

LFCASDAKAY DTEVHNVWAT HACVPTDPNP QEVVLGNVTE YFNMWKNNMV   100

DQMHEDIISL WDQSLKPCVK LTPLCVTLDC DDVNTTNSTT TTSNGWTGEI   150

RKGEIKNCSF NITTSIRDKV QKEYALFYNL DVVPIDDDNA TTKNKTTRNF   200

RLIHCNSSVM TQACPKVSFE PIPIHYCAPA GFAILKCNNK TFDGKGLCTN   250

VSTVQCTHGI RPVVSTQLLL NGSLAEEEVV IRSDNFMDNT KTIIVQLNES   300

VAINCTRPNN NTRKGIHIGP GRAFYAARKI IGDIRQAHCN LSRAQWNNTL   350

KQIVIKLREH FGNKTIKFNQ SSGGDPEIVR HSFNCGGEFF YCDTTQLFNS   400

TWNGTEGNNT EGNSTITLPC RIKQIINMWQ EVGKAMYAPP IGGQIRCSSN   450

ITGLLLTRDG GTEGNGTENE TEIFRPGGGD MRDNWRSELY KYKVVKVEPL   500

GVAPTRAKRR VVQR                                         514

SEQ ID NO: 7
       1 MRVMEIQRNC QHLLRWGIMI LGMIIICSTA DNLWVTVYYG VPVWRDAETT

51 LFCASDAKAY STEKHNVWAT HACVPTDPNP QEIPLDNVTE EFNMWKNNMV

101 DQMHEDIISL WDQSLKPCVQ LTPLCVTLNC SNARVNATFN STEDREGMKN

151 CSFNMTTELR DKKQQVYSLF YRLDIEKINS SNNNSEYRLV NCNTSAITQA

201 CPKVTFEPIP IHYCAPAGFA ILKCNDTEFN GTGPCKNVST VQCTHGIKPV

251 VSTQLLLNGS LAEREVRIRS ENIANNAKNI IVQFASPVKI NCIRPNNNTR

301 KSYRIGPGQT FYATDIVGDI RQAHCNVSRT DWNNTLRLVA NQLRKYFSNK

351 TIIFTNSSGG DLEITTHSFN CGGEFFYCNT SGLFNSTWTT NNMQESNDTS

401 NGTITLPCRI KQIIRMWQRV GQAMYAPPIE GVIRCESNIT GLILTRDGGN

451 NNSANETFRP GGGDIRDNWR SELYKYKVVK IEPLGVAPTR AKRRVVEREK

501 RAVGIGAVFL GFLGAAGSTM GAASITLTVQ ARQLLSGIVQ QQSNLLRAIE

551 AQQQLLKLTV WGIKQLQARV LAVERYLRDQ QLLGIWGCSG KLICTTNVPW

601 NSSWSNKSYD DIWQNMTWLQ WDKEISNYTD IIYSLIEESQ NQQEKNEQDL

651 LALDKWANLW NWFDISKWLW YIRS
```

SEQ ID NO: 8

```
   1  MGARASVLSG GELDRWEKIR LRPGGKKKYK LKHIVWASRE LERFAVNPGL
  51  LETSEGCRQI LGQLQPSLQT GSEELRSLYN TVATLYCVHQ RIEIKDTKEA
 101  LDKIEEEQNK SKKKAQQAAA DTGHSNQVSQ NYPIVQNIQG QMVHQAISPR
 151  TLNAWVKVVE EKAFSPEVIP MFSALSEGAT PQDLNTMLNT VGGHQAAMQM
 201  LKETINEEAA EWDRVHPVHA GPIAPGQMRE PRGSDIAGTT STLQEQIGWM
 251  TNNPPIPVGE IYKRWIILGL NKIVRMYSPT SILDIRQGPK EPFRDYVDRF
 301  YKTLRAEQAS QEVKNWMTET LLVQNANPDC KTILKALGPA ATLEEMMTAC
 351  QGVGGPGHKA RVLMGPISPI ETVPVKLKPG MDGPKVKQWP LTEEKIKALV
 401  EICTEMEKEG KISKIGPENP YNTPVFAIKK KDSTKWRKLV DFRELNKRTQ
 451  DFWEVQLGIP HPAGLKKKKS VTVLDVGDAY FSVPLDEDFR KYTAFTIPSI
 501  NNETPGIRYQ YNVLPQGWKG SPAIFQSSMT KILEPFRKQN PDIVIYQYMD
 551  DLYVGSDLEI GQHRTKIEEL RQHLLRWGLT TPDKKHQKEP PFLKMGYELH
 601  PDKWTVQPIV LPEKDSWTVN DIQKLVGKLN WASQIYPGIK VRQLCKLLRG
 651  TKALTEVIPL TEEAELELAE NREILKEPVH GVYYDPSKDL IAEIQKQGQG
 701  QWTYQIYQEP FKNLKTGKYA RMRGAHTNDV KQLTEAVQKI TTESIVIWGK
 751  TPKFKLPIQK ETWETWWTEY WQATWIPEWE FVNTPPLVKL WYQLEKEPIV
 801  GAETFYVDGA ANRETKLGKA GYVTNRGRQK VVTLTDTTNQ KTELQAIYLA
 851  LQDSGLEVNI VTDSQYALGI IQAQPDQSES ELVNQIIEQL IKKEKVYLAW
 901  VPAHKGIGGN EQVDKLVSAG IRKVLMVGFP VTPQVPLRPM TYKAAVDLSH
 951  FLKEKGGLEG LIHSQRRQDI LDLWIYHTQG YFPDWQNYTP GPGVRYPLTF
1001  GWCYKLVPVE PDKVEEANKG ENTSLLHPVS LHGMDDPERE VLEWRFDSRL
1051  AFHHVARELH PEYFKNC
```

SEQ ID NO: 9

```
atggttatcgtgcagaacatccaggggcaaatggtacatcaggccatatcacctagaactttaaatgcatggg
taaaagtagtagaagagaaggctttcagcccagaagtaatacccatgttttcagcattatcagaaggagccac
cccacaagatttaaacaccatgctaaacacagtggggggacatcaagcagccatgcaaatgttaaaagagacc
atcaatgaggaagctgcagaatgggatagagtacatccagtgcatgcagggcctattgcaccaggccagatga
gagaaccaaggggaagtgacatagcaggaactactagtacccttcaggaacaaataggatggatgacaaataa
tccacctatcccagtaggagaaatttataaaagatggataatcctgggattaaataaaatagtaagaatgtat
agccctaccagcattctggacataagacaaggaccaaaagaacctttagagactatgtagaccggttctata
aaactctaagagccgagcaagcttcacaggaggtaaaaaattggatgacagaaaccttgttggtccaaaatgc
gaacccagattgtaagactattttaaaagcatgggaccagcggctacactagaagaaatgatgacagcatgt
cagggagtaggaggacccggccataaggcaagagttttgcatatgggcccattagccctattgagactgtgt
cagtaaaattaaagccaggaatggatggcccaaaagttaaacaatggccattgacagaagaaaaaataaaagc
attagtagaaatttgtacagagatggaaaaggaagggaaaatttcaaaaattgggcctgaaaatccatacaat
actccagtatttgccataaagaaaaaagacagtactaaatggagaaaattagtagatttcagagaacttaata
agagaactcaagacttctgggaagttcaattaggaataccacatcccgcagggttaaaaaagaaaaaatcagt
aacagtactggatgtgggtgatgcatattttcagttcccttagatgaagacttcaggaaatatactgcattt
accataccagtataaacaatgagacaccagggattagatatcagtacaatgtgcttccacagggatggaaag
gatcaccagcaatattccaaagtagcatgacaaaaaatcttagagccttttagaaaacaaaatccagacatagt
```

-continued

```
tatctatcaatacatggatgatttgtatgtaggatctgacttagaaatagggcagcatagaacaaaaatagag gagctgagacaacatctgttgaggtggggacttaccacaccagacaaaaaacatcagaaagaacctccattcc ttaaaatgggttatgaactccatcctgataaatggacagtacagcctatagtgctgccagaaaaagacagctg gactgtcaatgacatacagaagttagtggggaaattgaattgggcaagtcagatttacccagggattaaagta aggcaattatgtaaactccttagaggaaccaaagcactaacagaagtaataccactaacagaagaagcagagc tagaactggcagaaaacagagagattctaaaagaaccagtacatggagtgtattatgacccatcaaaagactt aatagcagaaatacagaagcaggggcaaggccaatggacatatcaaatttatcaagagccatttaaaaatctg aaaacaggaaaatatgcaagaatgaggggtgcccacactaatgatgtaaaacaattaacagaggcagtgcaaa aaataaccacagaaagcatagtaatatggggaaagactcctaaatttaaactgcccatacaaaaggaaacatg ggaaacatggtggacagagtattggcaagccacctggattcctgagtgggagtttgttaataccctcccttta gtgaaattatggtaccagttagagaaagaacccatagtaggagcagaaaccttctatgtagatggggcagcta acagggagactaaattaggaaaagcaggatatgttactaatagaggaagacaaaaagttgtcaccctaactga cacaacaaatcagaagactgagttacaagcaatttatctagctttgcaggattcgggattagaagtaaacata gtaacagactcacaatatgcattaggaatcattcaagcacaaccagataaagtgaatcagagttagtcaatc aaataatagagcagttaataaaaaaggaaaaggtctatctggcatgggtaccagcacacaaaggaattggagg aaatgaacaagtagataaattagtcagtgctggaatcaggaaagtgcta[gctatg]ggtggcaagtggtcaaaa
``` agtagtgtggttggatggcctactgtaagggaaagaatgagacgagctgagccagcagcagatggggtgggag cagcatctcgagacctggaaaaacatggagcaatcacaagtagcaatacagcagctaccaatgctgcttgtgc ctggctagaagcacaagaggaggaggaggtgggttttccagtcacacctcaggtacctttaagaccaatgact tacaaggcagctgtagatcttagccactttttaaaagaaaagggggggactggaagggctaattcactcccaac gaagacaagatatccttgatctgtggatctaccacacacaaggctacttccctgattggcagaactacacacc agggccaggggtcagatatccactgacctttggatggtgctacaagctagtaccagttgagccagataaggta gaagaggccaataaaggagagaacaccagcttgttacacccctgtgagcctgcatggaatggatgaccctgaga gagaagtgttagagtggaggtttgacagccgcctagcatttcatcacgtggcccgagagctgcatccggagta cttcaagaactgc[aggcct]atgggtgcgagagcgtcagtattaagcgggggagaattagatcgatgggaaaaa attcggttaaggccaggggggaaagaaaaaatataaattaaaacatatagtatgggcaagcagggagctagaac gattcgcagttaatcctggcctgttagaaacatcagaaggctgtagacaaatactgggacagctacaaccatc ccttcagacaggatcagaagaacttagatcattatataatacagtagcaaccctctattgtgtgcatcaaagg atagagataaaagacaccaaggaagctttagacaagatagaggaagagcaaaacaaaagtaagaaaaagcac agcaagcagcagctgacacaggacacagcaatcaggtcagccaaaattactaa

SEQ ID NO: 10

| | |
|---|---|
| MVIVQNIQGQMVHQAISPRTLNAWVKVVEEKAFSPEVIPMFSALSEGATP | 50 |
| QDLNTMLNTVGGHQAAMQMLKETINEEAAEWDRVHPVHAGPIAPGQMREP | 100 |
| RGSDIAGTTSTLQEQIGWMTNNPPIPVGEIYKRWIILGLNKIVRMYSPTS | 150 |
| ILDIRQGPKEPFRDYVDRFYKTLRAEQASQEVKNWMTETLLVQNANPDCK | 200 |
| TILKALGPAATLEEMMTACQGVGGPGHKARVLHMGPISPIETVSVKLKPG | 250 |
| MDGPKVKQWPLTEEKIKALVEICTEMEKEGKISKIGPENPYNTPVFAIKK | 300 |
| KDSTKWRKLVDFRELNKRTQDFWEVQLGIPHPAGLKKKKSVTVLDVGDAY | 350 |
| FSVPLDEDFRKYTAFTIPSINNETPGIRYQYNVLPQGWKGSPAIFQSSMT | 400 |
| KILEPFRKQNPDIVIYQYMDDLYVGSDLEIGQHRTKIEELRQHLLRWGLT | 450 |
| TPDKKHQKEPPFL**※**MGYELHPDKWTVQPIVLPEKDSWTVNDIQKLVGKLN | 500 |

```
WASQIYPGIKVRQLCKLLRGTKALTEVIPLTEEAELELAENREILKEPVH      550

GVYYDPSKDLIAEIQKQGQGQWTYQIYQEPFKNLKTGKYARMRGAHTNDV      600

KQLTEAVQKITTESIVIWGKTPKFKLPIQKETWETWWTEYWQATWIPEWE      650

FVNTPPLVKLWYQLEKEPIVGAETFYVDGAANRETKLGKAGYVTNRGRQK      700

VVTLTDTTNQKTELQAIYLALQDSGLEVNIVTDSQYALGIIQAQPDQSES      750

ELVNQIIEQLIKKEKVYLAWVPAHKGIGGNEQVDKLVSAGIRKVLAMGGK      800

WSKSSVVGWPTVRERMRRAEPAADGVGAASRDLEKHGAITSSNTAATNAA      850

CAWLEAQEEEEVGFPVTPQVPLRPMTYKAAVDLSHFLKEKGGLEGLIHSQ      900

RRQDILDLWIYHTQGYFPDWQNYTPGPGVRYPLTFGWCYKLVPVEPDKVE      950

EANKGENTSLLHPVSLHGMDDPEREVLEWRFDSRLAFHHVARELHPEYFK      1000

NCREMGARASVLSGGELDRWEKIRLRPGGKKKYKLKHIVWASRELERFAV      1050

NPGLLETSEGCRQILGQLQPSLQTGSEELRSLYNTVATLYCVHQRIEIKD      1100

TKEALDKIEEQNKSKKKAQQAAADTGHSNQVSQNY                    1136
```

SEQ ID NO: 11
```
   1  MAARASILSG GKLDAWEKIR LRPGGKKKYR LKHLVWASRE LDRFALNPSL
  51  LETTEGCQQI MNQLQPAVKT GTEEIKSLFN TVATLYCVHQ RIDVKDTKEA
 101  LDKIEEIQNK SKQKTQQAAA DTGDSSKVSQ NYPIIQNAQG QMIHQNLSPR
 151  TLNAWVKVIE EKAFSPEVIP MFSALSEGAT PQDLNVMLNI VGGHQAAMQM
 201  LKDTINEEAA EWDRLHPVQA GPIPPGQIRE PRGSDIAGTT STPQEQLQWM
 251  TGNPPIPVGN IYKRWIILGL NKIVRMYSPV SILDIKQGPK EPFRDYVDRF
 301  FKALRAEQAT QDVKGWMTET LLVQNANPDC KSILKALGSG ATLEEMMTAC
 351  QGVGGPGHKA RVLAEAMSQA QQTNIMMQRG NFRGQKRIKC FNCGKEGHLA
 401  RNCRAPRKKG CWKCGKEGHQ MKDCTERQAN FLGKIWPSSK GRPGNFPQSR
 451  PEPTAPPAEL FGMGEGIASL PKQEQKDREQ VPPLVSLKSL FGNDPLSQGS
 501  PISPIETVPV TLKPGMDGPK VKQWPLTEEK IKALTEICTE MEKEGKISKI
 551  GPENPYNTPI FAIKKKDSTK WRKLVDFREL NKRTQDFWEV QLGIPHPAGL
 601  KKKKSVTVLD VGDAYFSVPL DENFRKYTAF TIPSTNNETP GVRYQYNVLP
 651  QGWKGSPAIF QSSMTKILEP FRSKNPEIII YQYMAALYVG SDLEIGQHRT
 701  KIEELRAHLL SWGFTTPDKK HQKEPPFLWM GYELHPDKWT VQPIMLPDKE
 751  SWTVNDIQKL VGKLNWASQI YAGIKVKQLC RLLRGAKALT DIVTLTEEAE
 801  LELAENREIL KDPVHGVYYD PSKDLVAEIQ KQGQDQWTYQ IYQEPFKNLK
 851  TGKYARKRSA HTNDVRQLAE VVQKVAMESI VIWGKTPKFK LPIQKETWET
 901  WWMDYWQATW IPEWEFVNTP PLVKLWYQLE KDPILGAETF YVDGAANRET
 951  KLGKAGYVTD RGRQKVVSLT ETTNQKTELH AILLALQDSG SEVNIVTDSQ
1001  YALGIIQAQP DRSESELVNQ IIEKLIGKDK IYLSWVPAHK GIGGNEQVDK
1051  LVSSGIRKVL FLDGIDKAQE DHERYHSNWR TMASDFNLPP IVAKEIVASC
1101  DKCQLKGEAM HGQVDCSPGI WQLACTHLEG KVILVAVHVA SGYIEAEVIP
1151  AETGQETAYF LLKLAGRWPV KVVHTANGSN FTSAAVKAAC WWANIQQEFG
1201  IPYNPQSQGV VASMNKELKK IIGQVRDQAE HLKTAVQMAV FIHNFKRKGG
1251  IGGYSAGERI IDIIATDIQT KELQKQITKI QNFRVYYRDS RDPIWKGPAK
```

```
1301 LLWKGEGAVV IQDNSDIKVV PRRKAKILRD YGKQMAGDDC VAGRQDEDRS

1351 MGGKWSKGSI VGWPEIRERM RRAPAAAPGV GAVSQDLDKH GAITSSNINN

1401 PSCVWLEAQE EEEVGFPVRP QVPLRPMTYK GAFDLSHFLK EKGGLDGLIY

1451 SRKRQEILDL WVYHTQGYFP DWQNYTPGPG VRYPLTFGWC FKLVPMEPDE

1501 VEKATEGENN SLLHPICQHG MDDEEREVLI WKFDSRLALK HRAQELHPEF

1551 YKDC
```

SEQ ID NO: 12

Protein D_H influenzae

```
  (1) MKLKTLALSLLAAGVLAGCSSHSSNMANTQMKSDKIIIAHRGASGYLPEH

51)  TLESKALAFAQQADYLEQDLAMTKDGRLVVIHDHFLDGLTDVAKKFPHRH (101) RKDGRYYVIDFTLKEIQSLEMTENFET
```

---

The invention claimed is:

1. A method of making a lyophilised composition for use in a reconstitution solution said method comprising the steps of: mixing WT-1 antigen having an isoelectric point which is lower than the pH of the reconstitution solution and TLR9 agonist, and submitting the resulting formulation to a lyophilisaton cycle.

2. A method of making an immunogenic composition comprising the steps of reconstituting a lyophilised composition according to claim 1 with a suitable carrier.

3. A method according to claim 2 wherein said carrier is selected from the group consisting of mineral salts, emulsions, polymers, liposomes, ISCOMs.

4. A method according to claim 3 wherein said carrier is a liposomal solution or an oil in water emulsion.

5. A method according to claim 2 wherein said carrier further comprises one or more immunostimulants.

6. A method according to claim 5 wherein said one or more immunostimulants are selected from the group consisting of TLR 4 agonists, saponins, TLR7 agonists and TLR8 agonists.

7. A method according to claim 6 wherein said TLR 4 agonist is 3-deacylated MPL.

8. A method according to claim 6 wherein one of said saponins is QS21.

9. A method according to claim 4 wherein said carrier comprises two immunostimulants.

10. A method according to claim 9 wherein said immunostimulants are 3-deacylated MPL and QS21.

11. A method according to claim 2 wherein the TLR9 agonist comprises a CpG-containing immunostimulatory oligonucleotide.

12. A method according to claim 11 wherein the CpG-containing immunostimulatory oligonucleotide is selected from the group consisting of: SEQ ID NO 1, SEQ ID NO 2, SEQ ID NO 3, SEQ ID NO 4 and SEQ ID NO 5.

13. A method according to claim 1 wherein the WT-1 antigen is a recombinant fusion protein consisting of a tat sequence and amino acids number 2-281 of the WT1 sequence.

14. A method of making a composition comprising a WT-1 antigen and a TLR9 agonist, said method comprising the steps of: mixing WT-1-A10 antigen having an isoelectric point between 5.858 and 7.5 and a CpG-containing immunostimulatory oligonucleotide selected from the group consisting of: SEQ ID NO 1, SEQ ID NO 2, SEQ ID NO 3, SEQ ID NO 4 and SEQ ID NO 5, and submitting the resulting formulation to a lyophilisaton cycle.

15. The method of claim 14 further comprising the step of reconstituting the lyophilised composition in the reconstitution solution with a pH that renders the WT-1 antigen non-positively charged.

16. The method of claim 1 wherein the isoelectric point is between 5.85 and 7.5.

17. The method of claim 1 wherein the reconstitution solution has a pH of 6.1.

18. A method of making an immunogenic composition for use in a reconstituting solution comprising the steps of:
   mixing WT-1 antigen and CpG-containing immunostimulatory oligonucleotide TLR9 agonist,
   submitting the resulting formulation to a lyophilisaton cycle, and
   reconstituting the lyophilised composition in a reconstitution solution having a pH which is higher than the isoelectric point of the WT-1 antigen.

19. The method of claim 18 wherein the CpG-containing immunostimulatory oligonucleotide is selected from the group consisting of: SEQ ID NO 1, SEQ ID NO 2, SEQ ID NO 3, SEQ ID NO 4 and SEQ ID NO 5.

20. The method of claim 18 wherein the WT-1 antigen is WT-1-A10.

* * * * *